US006977767B2

(12) United States Patent
Sarychev et al.

(10) Patent No.: US 6,977,767 B2
(45) Date of Patent: Dec. 20, 2005

(54) PLASMONIC NANOPHOTONICS METHODS, MATERIALS, AND APPARATUSES

(75) Inventors: Andrey K. Sarychev, West Lafayette, IN (US); Vladimir M. Shalaev, West Lafayette, IN (US); Alexander M. Dykhne, Moscow Region (RU); Viktor A. Podolskiy, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 416 days.

(21) Appl. No.: 10/132,606

(22) Filed: Apr. 25, 2002

(65) Prior Publication Data

US 2003/0042487 A1 Mar. 6, 2003

Related U.S. Application Data

(60) Provisional application No. 60/286,437, filed on Apr. 25, 2001, and provisional application No. 60/330,059, filed on Oct. 16, 2001.

(51) Int. Cl.[7] .................................................. G02F 1/00
(52) U.S. Cl. ...................... 359/321; 359/290; 359/291
(58) Field of Search .......................... 359/238, 321–323, 359/245–246, 240, 248, 251–252, 255, 262, 281–282, 290–291, 293–4, 297

(56) References Cited

U.S. PATENT DOCUMENTS

| | | | |
|---|---|---|---|
| 4,006,963 A | 2/1977 | Baues et al. | 385/37 |
| 4,528,464 A | 7/1985 | Chemia et al. | 359/326 |
| 4,659,429 A | 4/1987 | Isaacson et al. | 216/24 |
| 4,900,134 A | 2/1990 | Inoue et al. | 359/241 |
| 5,016,990 A | 5/1991 | Dobson | 359/260 |
| 5,155,617 A | 10/1992 | Solgaard et al. | 359/245 |
| 5,182,665 A | 1/1993 | O'Callaghan et al. | 249/201 |
| 5,466,925 A | 11/1995 | Hait | 250/216 |
| 5,485,014 A | 1/1996 | Jain et al. | 257/21 |
| 5,504,772 A | 4/1996 | Deacon et al. | 372/102 |
| 5,698,863 A | 12/1997 | Pelekanos | 257/21 |
| 5,789,742 A | 8/1998 | Wolff | 250/227.11 |
| 5,969,345 A | 10/1999 | Williams et al. | 250/234 |
| 5,973,316 A | 10/1999 | Ebbesen et al. | 250/216 |
| 6,040,936 A | 3/2000 | Kim et al. | 359/245 |
| 6,172,793 B1 | 1/2001 | Heberle et al. | 359/264 |
| 6,236,033 B1 | 5/2001 | Ebbesen et al. | 250/216 |
| 6,285,020 B1 | 9/2001 | Kim et al. | 250/216 |
| 6,538,794 B1 * | 3/2003 | D'Aguanno et al. | 359/279 |
| 6,597,492 B1 * | 7/2003 | Rosenman et al. | 359/326 |
| 6,791,736 B2 * | 9/2004 | Jain | 359/261 |
| 6,795,198 B1 * | 9/2004 | Fuchs et al. | 356/521 |

OTHER PUBLICATIONS

Sarychev, A.K., et al., "Electromagnetic Field Fluctuations and Optical Nonlinearities in Metal–Dielectric Composites," *Physics Reports*, vol. 335, pp 275–371 (2000).

Ashrift, P.V., et al., "Dielectric Constants of Silver Particles Finely Dispersed in a Gelatin Films" *J. Appl. Phys.*, vol. 74, No. 1, PP 602–606 (Jul. 1, 1993).

Bennett, P.J., et al., "Femtosecond Cubic Optical Nonlinearity of Thin Nickel Films," *Optics Letters*, vol. 24, No. 19, pp 1373–1375 (Oct. 1, 1999).

(Continued)

*Primary Examiner*—Jordan M. Schwartz
*Assistant Examiner*—Jessica Stultz
(74) *Attorney, Agent, or Firm*—Peacock Myers & Adams; Deborah A. Peacock; Jeffrey D. Myers

(57) ABSTRACT

Controlling, guiding, manipulating, and circuiting light and performing surface-enhanced spectroscopy in a medium comprising plasmonic nanomaterials via the excitation of plasmon modes in the materials. The plasmonic nanomaterials are based on metal films with or without arrays of nanoholes and/or on metal nanowires and/or spheroids. Also devices and methods employing such plasmonic nanomaterials.

44 Claims, 15 Drawing Sheets

OTHER PUBLICATIONS

Ebbesen, T.W., et al., "Extraordinary Optical Transmission Through Sub-Wavelength Hole Arrays," *Nature*, vol. 391, pp 667–669(Feb. 12, 1998).

Dubrus, S., et al., "Z-Scan Determination of the Third-Order Optical Nonlinearity of Gold:Silica Nanocomposites," *J. Appl. Phys.*, vol. 88, No. 8, pp 4469–4475 (Oct. 15, 2000).

Dogaiu, A. et al., "Delay in Light Transmission Through Small Apertures," *Optics Ltrs.*, vol. 26, No. 7, pp 450–452 (Apr. 1, 2001).

Ducourtieux, S., et al., "Near-Field Optical Studies of Semicontinuous Metal Films," *Phys. Review B*, vol. 64 165403, pp 1–14 (2001).

Freilikher, V., et al., "Coherent Scattering Enhancement in Systems Bounded by Rough Surfaces," *Phys. Reports*, vol. 288, pp 127–204 (1997).

Ghaemi, H.F., "Surface Plasmons Enhance Optical Transmission Through Subwavelength Holes," *Phys. Review B*, vol. 58, No. 11, pp 6779–6782 (Sep. 15, 1998).

Grupp, D.E. et al., "Crucial Roles of Metal Surfaces in Enhanced Transmission Through Subwavelength Apertures," *Appl. Phys. Ltrs.*, vol. 77, No. 11, pp 1569–1571 (Sep. 11, 2000).

Hibbins, A.P., et al., "Grating-Coupled Surface Plasmons at Microwave Frequencies," *J Appl Phys.*, vol. 86, No. 4, p 1791–1795) Aug. 15, 1999).

Kim, T.J., et al., "Control of Optical Transmission Through Metals Perforated with Subwavelength Hole Arrays," *Optics Letters*, vol. 24, No. 4, pp 256–258 (Feb. 15, 1999).

Lagarkov, A.N., et al., "Electromagnetic Properties of Composites Containing Elongated Conducting Inclusions," *Phys. Review B*, vol. 53, No. 10, pp 6318–6336 (Mar. 1, 1996–II).

Largarkov, A.N., et al., "Experimental and Theoretical Study of Metal-Dielectric Percolating Films at Microwaves," *Physica A*, vol. 24, pp 199–206 (1997).

Landau, L.D., et al., "Electrodynamics of Continuous Media," *Vol. 8 of Course of Theoretical Physics*, Butterworth-Heinemann Publishers, $2^{nd}$ Ed. (Pergamon, Oxford 1984).

Levy-Nathansohn, R., et al., "Studies of the Generalized Ohm's Law," *Physica A*, vol. 241, pp. 166–172 (1997).

Levy-Nathansohn, R., et al., "Decoupling and Testing of the Generalized Ohm's Law," *Phys. Rev. B*, vol. 55, No. 8, pp 5425–5439 (Feb. 15, 1997–II).

Martin-Moreno, L., et al., "Theory of Extraordinary Optical Transmission Through Subwavelength Hole Arrays," *Phys. Rev. Letters*, vol. 86, No. 6, pp 1114–1117 (Feb. 5, 2001).

Nash, D.J., et al., "Surface Plasmon-Polariton Study of the Optical Dielectric Function of Silver," *Modern Optics*, vol. 43, No. 1, pp 81–91 (1996).

Nash, D.J., et al., "Simultaneous Observation of Surface Plasmons on Both Sides of Thin Silver Films," *J. Modern Optics*, vol. 46, No. 12, pp 1793–1800 *1999).

Nolte, D.D., et al., "Photorefractive Semiconductor Nanostructures," *Handbook of Nanostructured Materials and Nanotechnology*, H.S. Nalwa, Ed. (Academic Press, San Diego 2000).

Pendry, J.B., et al., "Extremely Low Frequency Plasmons in Metallic Mesostructures," *Phys. Review Ltrs.*, vol. 76, No. 25, pp 4773–4776 (Jun. 17, 1996).

Raether, H., "Surface Plasmons on Smooth and Rough Surfaces and on Gratings" Springer, Berlin 1988 pp 1–135 (1988).

Rayleigh, B., et al., "The Theory of Sound", $2^{nd}$ Ed. MacMillan, London, 1896).

Salomon, L., et al., "Near-Field Distribution of Optical Transmission of Periodic Subwave-length Holes in a Metal Film," *Phys. Rev. Ltrs.*, vol. 86, No. 6, pp 1110–1113 (Feb. 5, 2001).

Sarychev, A.K., et al., "Theory of the Optical and Microwave Properties of Metal-Dielectric Films," *Phys. Rev. B*, vol. 51, No. 8, pp 5366–5385, (Feb. 15, 1995–II).

Sarychev, A.K., et al., "Optical and Microwave Properties of Metal-Insulator Thin Films: Possibility of Light Localization," *Physica A*, vol. 207, pp 372–378 (1994).

Sarychev, A.K., et al., "Electrodynamics of Metal-Dielectric Composites and Electromagnetic Crystals," *Phys. Review B*, vol. 62, No. 12, pp 8531–8539 (Sep. 15, 2000–II).

Sarychev, A.K., et al., "Electromagnetic Field Fluctuations and Optical Nonlinearities in Metal-Dielectric Composites," *Phys. Reports*, vol. 335, pp 275–371 (2000).

Shubin, V.A., et al., "Local Electric and Magnetic Fields in Semicontinuous Metal Films: Beyond the Quasistatic Approximation," *Phys. Review B*, vol. 62, No. 16, pp 11–230–11–244, (Oct. 15, 2000–II).

Sievenpiper, D.F., et al., "3D Wire Mesh Photonic Crystals," *Phys Review Ltrs*, vol. 76, No. 14, pp 2480–2483 (Apr. 1, 1996).

Sonnichsen, C., et al., "Laundhing Surface Plasmons into Nanoholes in Metal Films," *Appl. Phys. Ltrs.*, vol. 76, No. 2, pp 140–142 (Jan. 10, 2000).

Tan, W.-C., et al., "Flat-Surface-Plasmon-Polariton Bands and Resonant Optical Absorption on Short-Pitch Metal Gratings," *Phys. Review B*, vol. 59, No. 19, pp 12–661–12–666 (May 15, 1999–I).

Tan, W.-C., et al., "Resonant Tunneling of Light Through Thin Metal Films Via Strongly Localized Surface Plasmons," *Phys. Review B*, vol. 62, No. 16, pp 11–134–11–138 (Oct. 15, 2000–II).

Wannemacher, R., et al., "Plasmon-Supported Transmission of Light Through Nanometric Holes in Metallic Thin Films," *Optics Comm.*, vol. 195, pp 107–118 (2001).

V. M. Shalaev, *Nonlinear Optics of Random Media; Fractal Composites and Metal-Dielectric Films*, Springer Tracts in Modern Physics, v.158, Springer, Berlin Heidelberg 2000.

A. K. Sarychev and V. M. Shalaev, "Field Distribution, Anderson localization, and optical phenomena in random metal-dielectric films," Chapter in: *Optics of Nanostructured Materials*, Eds: V.A. Markel and T.F. George, Wiley, 2001.

V.M. Shalaev, "Surface-Enhanced Optical Phenomena in Nanostructured Fractal Materials," Chapter in: *Handbook of Nanostructured Materials and Nanotechnology*, vol. 4: Optical Properties, Edited by H.S. Nalwa, Academic Press, 2000.

V. M. Shalaev, V. P. Safonov, E.Y. Poliakov, V. A. Markel, and A. K. Sarychev, "Fractal Surface Enhanced Optical Nonlinearities", Chapter 8: *Nanostructured Materials: Clusters, Composites, and Thin Films*, Eds; V. M. Shalaev and M. Moskovits, ACS Symposium Series v. 679, ACS Books, 1997.

Local Field Distribution in Random Metal-Dielectric Films; Theory and Experiment, Dentcho A. Genov, Katyatani Seal, Mark A. Nelson, Andrey K. Sarychev, Z. Charles Ying, Vladimir M. Shalaev, Physica B 338, pp. 228–231 (2003).

Metal coverage dependence of local optical properties of semicontinuous metal films, K. Seal, M. A. Nelson, Z. C. Ying, D. A. Genov, A. K. Sarychev, and V. M. Shalaev, J. of Modern Optics 49, 2423–2435 (2002).

V. A. Podolskiy, A. K. Sarychev, V. M. Shalaev, "Temporal Dynamics of Local Optical Responses and Sub–fs Pulse Generation in Semicontinuous Metal Films," Laser Physics 12, 292 (2002).

M. Breit, V. A. Podolskiy, S. Gresillon, G. von Plessen, J. Feldman, J. C. Rivoal, P. Gadenne, A. K. Sarychev, and Vladimir M. Shalaev, *Experimental observation of percolation–enhanced non–linear light scattering*, Phys. Rev. B 64, 125106 (2001).

V. A. Podolskiy, A. K. Sarychev, and Vladimir M. Shalaev, Percolation Composites: Localization of Surface Plasmons and Enhanced Optical Nonlinearities, in Photonic Crystals and Light Localization in the 21st Century, 567, ed. by C. M. Soukoulis (Kluwer Academic Publishers, 2001).

M. Gadenne, V. Podolskiy, P. Gadenne, P. Sheng and V. M. Shalaev, Plasmon–enhanced absorption by optical phonons in metal–dielectric composites, Europhys. Lett. 53, 364 (2001).

V.M. Shalaev and Z. C. Ying, Nonlinear Optics of Surfaces, Encyclopedia of Materials: Science and Technology, ed. by D. D. Nolte (Pergamon, Amsterdam 2000), article 6.8.13.

V. A. Shubin, A.K.Sarychev, J. P. Clerc, and V.M.Shalaev, *Local Electric And Magnetic Fields In Semicontinuous Metal Films*, Phys. Rev. B62, 11230 (2000).

A. K. Sarychev, A. A. Shubin, V. M. Shalaev, Anderson localization of surface plasmons and Kerr nonlinearity in semicontinuous metal Films, Physica B 279, 87 (2000).

A. K. Sarychev, P. C. McPhedran, and V. M. Shalaev, *Electrodynamics of metal–dielectric composites and electromagnetic crystals*, Phys. Rev. B 62, 8531 (2000).

S. Ducourtieux, S. Gresillon, A. C. Boccara, J. C. Rivoal, X. Quelin, P. Gaddene, V. P. Drachev, W. D. Bragg, V. P. Safonov, V. A. Podolskiy, Z. C. Ying, R. L. Armstrong, and Vladimir M. Shalaev, Percolation and Fractal Composites: Optical Studies, J. of Nonlinear Optical Physics and Materials 9, 105 (2000).

S. Gresillon, L. Aigouy, A. C. Boccara, J. C. Rivoal, X. Quelin, C. Desmarest, P. Gadenne, V. A. Shubin, A. K. Sarychev, and V. M. Shalaev, Experimental Observation of Localized Optical Excitations in Random Metal–Dielectric Films, Phys. Rev. Lett. 82, 4520 (1999).

W. Kim, V. P. Safonov,V. M. Shalaev,R. L. Armstrong, Fractals in Microcavities: Giant Coupled Multiplicative Enhancement of Optical Responses, Phys. Rev. Lett. 82, 4811 (1999).

A. K. Sarychev, V. A. Shubin, and Vladimir M. Shalaev, Anderson localization of surface plasmons and nonlinear optics of metal–dielectric composites, Phys. Rev. B 60, 16389 (1999).

V. A. Shubin, W. Kim, V. P. Safonov, A. K. Saruchev, R. L. Armstrong, and Vladimir M. Shalaev, Surface–Plasmon–Enhanced Radiation Effects in Confined Photonic Systems, J. of Lightwave Technology 17, 2183 (1999).

E. Poliakov, V. M. Shalaev, V. Shubin, V. A. Markel, Enhancement of nonlinear processes near rough nanometer–structured surfaces obtained by deposition of fractal colloidal aggregates on a plain substrate, Phys. Rev. B 60, 10739 (1999).

N. N. Lepeshkin, W. Kim, V. P. Safonov,J. G. Zhu,R. L. Armstrong,C. W. White,R. A. Zuhr, and V. M. Shalaev, Optical Nonlinearities of Metal–Dilectric Composites, J. of Nonlinear Optical Physics and Materials 8, 191 (1999).

Vladimir M. Shalaev and Andrey K. Sarychev, Nonlinear optics of random metal–dielectric films, Phys. Rev. B 57, 13265 (1998).

S. I. Bozhevolnyi, V. A. Markel, V. Coello, W. Kim, and V. M. Shalaev, Direct Observation of Localized Excitations on Rough Nanostructured Surfaces, Phys. Rev. B 58, 11441 (1998).

V.M. Shalaev, V. A. Markel,E.Y.Poliakov, R. L. Armstrong, V. P. Safonov,A. K. Sarychev, Nonlinear Optical Phenomena in Nanostructured Fractal Materials, J. Nonlinear Optic. Phys. and Materials, v. 7, 131 (1998).

V. M. Shalaev, E. Y. Poliakov, V. A. Markel, R. Botet, Nonlinear optics of fractal nanomaterials: Small–particle composites and self–affine thin Films, Physica A 241, 249 (1997).

V. M. Shalaev, E. Y. Poliakov, V.A.Markel, R. Botet,E. B. Stechel,Optical properties of self–affine surfaces, in: Fractal Frontiers, Eds: M. M. Novak and T. G. Dewey, World Scientific, Singapore, 1997; p. 421.

F. Brouers, S. Blacher,A.N. Lagarkov,A.K. Sarychev,P. Gadenne, V.M. Shalaev, Theory of giant Raman scattering from semicontinuous fims, Phys. Rev. B 55, 13234 (1997).

Vladimir M. Shalaev, E.Y. Poliakov, V.A. Markel, and R. Botet, Nonlinear Optics of Fractal Nanocompsites and Self–Affine Thin Films, Physica A 241, 249 (1997).

Vadim A. Markel, Vladimir M. Shalaev, Evgeni Y. Poliakov, Thomas F. George, Fluctuations of light scattered by fractal clusters, J.Opt.Soc.Amer., 14, 60 (1997).

Evgeni Y. Poliakov, Vladimir M. Shalaev, Vadim A. Markel, Robert Botet, Enhanced Raman scattering from self–affine thin films, Opt.Lett., 221, 1628 (1996).

Vladimir M. Shalaev, R. Botet, J. Mercer, and E.B. Stechel, Optical properties of self–affine thin films, Phys. Rev. B 54, 8235 (1996).

Vladimir M. Shalaev, Mark I. Stockman, and R. Botet, Resonant excitations and nonlinear optics of fractals, Physica A 185, 181 (1992).

Vladimir M. Shalaev, R. Botet, and R. Jullien, Erratum: Resonant light scattering by fractal clusters, Phys. Rev. B 45, 7592 (1992).

Vladimir M. Shalaev, R. Botet, and R. Jullien, Resonant light scattering by fractal clusters, Phys. Rev. B44, 12216 (1991).

A.V. Butenko, P.A. Chubakov, Yu.E. Danilova, S.V. Karpov, A.K. Popov, S.G. Rautian, V.P. Safonov, V.V. Slabko, V.M. Shalaev, and M.I.Stockman, Nonlinear optics of metal fractal clusters, Z.Phys.D– Atoms, Molecules and Clusters 17, 283 (1990).

P. Gadenne, B. Berini, S. Buil, X. Quelin, S. Gresillon, S. Ducourtieux, J.C. Rivoal, A. K. Sarychev, V. M. Shalaev, Localized plasmon–enhanced optical response: harmonic generation and polarization effects, Proceeding of SPIE's 46 Annual Meeting v. 4467, 288 (2001).

Vladimir M. Shalaev, Nonlinear Optics of Random Nanostructured Materials: Composites, Clusters, and Thin Films, XVI International Conference on Coherent and Nonlinear Optics (Moscow, Russia, Jun. 29–Jul. 3, 1998), ICONO.98 Technical Digest, URSS Publishers, p. 100 (1998).

V. M. Shalaev and A. K. Sarychev, Nonlinear Optics of Random Metal–Dielectric Films, in Nonlinear Optics.98. Materials, Fundamentals and Applications. Topical Meeting. Kauai, Hawaii, Aug. 10–14, 1998 IEEE Catalog No. 98CH36244, p. 22 (1998).

V. M. Shalaev, Fractal–surface–enhanced optical nonlinearities, Technical Digest of the Quantum Electronics and Laser Science Conference, QELS.97, Baltimore, May 18–23, 1997, 1997 OSA Technical Digest Series, v. 12, p. 88.

E. Poliakov, V. M. Shalaev, Nonlinear Optical Effects in Fractal Nanostructured Materials such as Nanocomposites and Self–Affine Surfaces, Chemistry and Physics of Small–Scale structures, Technical Digest Series, v. 2, Santa Fe, Feb. 9–11, 1997; p. 49.

R. L. Armstrong, V. P. Safonov, N. N. Lepeshkin, W. Kim, and V. M. Shalaev, Giant optical nonlinearities of fractal colloid aggregates, SPIE, San Diego, p. 107, 1997.

Vladimir M. Shalaev, Giant Optical Nonlinearities in Fractal Nanostructured Composites, Technical Digest, XX International Quantum Electronics Conference, Sydney (1996).

Vladimir M. Shalaev, J. Mercer, V.P. Safonov, and R. Botet, Nonlinear Optics of Fractal Nanocomposites and Self–Alline Surfaces, Technical Digest of Summer Topical Meeting, Nonlinear Optics: Materials, Fundamentals, and Applications, Maui, Hawaii, (1996).

V.A. Markel, E.B. Stechel, W. Kim, R. Armstrong, and Vladimir Shalaev, Optical Properties of fractal nanocomposites, Mat.Res.Soc Symp.Proc. vol. 367, 417 (1995).

Vladimir Shalaev, R. Botet, M. Moskovits, Subwavelength localization of optical modes in fractals, In: Molecular Designed Ultrafine Nanostructured Materials, Mat.Res.Soc Symp.Proc. vol. 351, 449 (1994).

A.V. Butenko, V.A. Markel, L.S. Muratov, V.M. Shalaev, and M.I. Stockman, Theory and Numerical Simulations of Optical Properties and Selective Photomodification of Fractal Clusters, Proc. X International Vavilov Conference on Nonlinear Optics; in: Nonlinear Optics, edited by S.G. Rautian, Nova Science Publishers, 275 (1992).

Yu, E. Danilova, S.V. Karpov, A.K. Popov, S.G. Rautian, V.P. Safonov, V.V. Slabko, V.M. Shalaev, and M.I. Stockman, Experimental Investigation of Optical Nonlinearities of Silver Fractal Clusters, Proc. X International Vavilov Conference on Nonlinear Optics; in: Nonlinear Optics, edited by S.G. Rautian, Nova Science Publishers, 295 (1992).

A.V. Butenko, P.A. Chubakov, Yu.E. Danilova, S.V. Karpov, A.K. Popov, S.G. Rautian, V.P. Safonov, V.V. Slabko, V.M. Shalaev, M.I. Stockman, Nonlinear Optics of Metal Fractal Clusters, in: Proc. International School on Lasers and Applications, Sayanogorsk, Eastern Siberia, USSR; Published by Institute for Physics, USSR Academy of Sci., Krasnoyarsk, 78 (1991).

V.M. Shalaev, M.I. Stockman, Optical properties of fractal clusters, Proc. 3–rd Int. Conf.Trends in Quantum Electronics., Romania, 201 (1988).

* cited by examiner

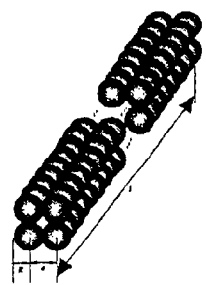
Fig. 17
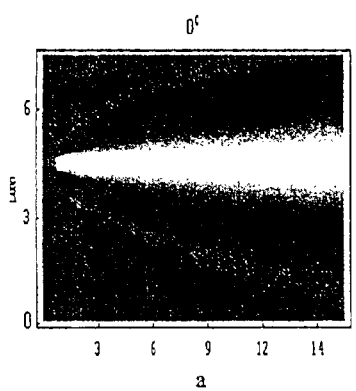
Fig. 18A
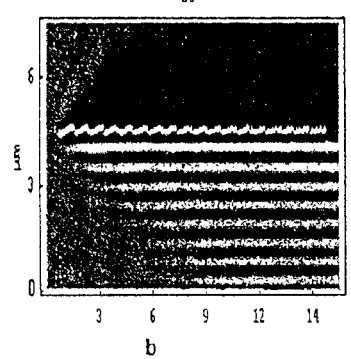
Fig. 18B
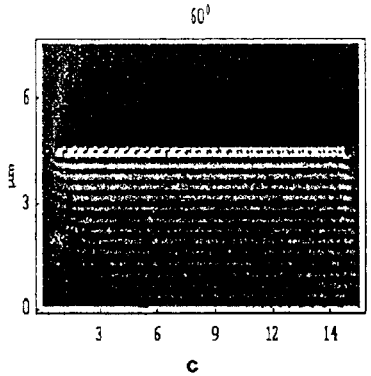
Fig. 18C
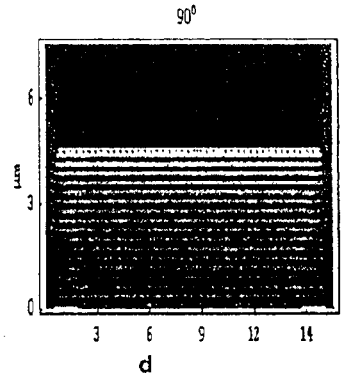
Fig. 18D
Fig. 18

PLASMONIC NANOPHOTONICS METHODS, MATERIALS, AND APPARATUSES

CROSS-REFERENCE TO RELATED APPLICATIONS

This application claims the benefit of the filing of U.S. Provisional Patent Application Ser. No. 60/286,437, entitled "Light-Controlled Extraordinary Optical Transmittance and Its Applications", filed on Apr. 25, 2001, and of the filing of U.S. Provisional Patent Application Ser. No. 60/330,059, entitled "Resonance Transmittance Through Metal Film with Subwavelength Holes", filed on Oct. 16, 2001, and the specifications thereof are incorporated herein by reference.

BACKGROUND OF THE INVENTION

1. Field of the Invention (Technical Field)

The present invention relates to methods and apparatuses employing plasmonic materials for extraordinary light transmittance through optically thick metal films and other ways to control light, particularly for use in optical devices.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

All-optical logic systems to replace semiconductor-based systems are becoming an increasingly important goal as the inherent physical limitations of electronic systems are approached. Stable and error-free optical components, including optical gates, optical switches, optical transistors, and optical filters, are required by such all-optical logic systems. The present invention provides such devices and underlying methods of accomplishment.

The existing art, represented by the following United States patent documents, are usefully divided into five groups:

1. Devices in which quantum wells are used to achieve manipulation of one laser beam by another.
2. Devices used to achieve great spatial resolution in optical object imaging.
3. Devices using arrays of subwavelength holes to achieve optical filtration or other related goals.
4. Electrooptical devices.
5. Amplitude to phase conversion logical devices.

Group 1 comprises U.S. Pat. Nos. 4,528,464, 5,485,014, 5,016,990, and 6,172,793. Each of these employ semiconductor quantum wells, which the present invention does not employ. Moreover, optical switches which are based on the confined Stark effect in quantum wells are much slower then switches which are based on the Kerr effect, as described in the present application.

Group 2 comprises U.S. Pat. Nos. 5,789,742, 5,969,345, and 4,659,429. The devices described obtain high spatial resolution when doing optical microscopy and lithography.

Group 3 comprises U.S. Pat. Nos. 6,040,936, 5,973,316, 6,236,033, and 6,285,020. The devices described use perforated metal films for selective optical transmittance, light intensity modulation, and related functions. However, all the devices described require holes (or modulation in the metal film) to be periodic. The present invention does not require any hole periodicity to achieve the goals of selective optical transition or related functions. The present invention depends only on the spatial periodicity of perturbation of refractive index, eliminating the need for periodically perforated metal films.

Group 4 comprises U.S. Pat. No. 5,155,617. The device described in the patent provides selective reflectance or absorbance controlled by applied electric field. As opposed to the present invention, this device is incapable of transmitting the light through it and of being controlled by another light pulse.

Group 5 comprises U.S. Pat. No. 5,466,925. The device described in this patent is used to convert amplitude-modulated input into phase-modulated output. Such a device is deemed to be capable of implementing AND, OR, and NAND operations for an optical computer. The device is not capable of optical circuiting, optical switching, or selective optical transmission.

SUMMARY OF THE INVENTION
(DISCLOSURE OF THE INVENTION)

The present invention is of a method for optically controlling characteristics of an optically thick metal film, comprising: providing a film with an optical nonlinearity but not having fabricated periodic perforation; and directing at the film at least two control light beams at angles $\pm\Theta$ with respect to normal; thereby inducing light transmittance through the film. In the preferred embodiment, one or more layers of highly nonlinear material may be employed on one or more sides of the film, which may be photorefractive semiconductor layers on one or more sides of the film. Inclusions of highly nonlinear material may be provided within the film, which may be photorefractive semiconductor inclusions. Two or more control beams may be directed to each side of the film. Directing may comprise switching on and off the control beams. A periodic or non-periodic modulation may be applied to the control beams. The induced light transmittance may have two or more stable states, any of which states may be induced. Non-linearity may be generated by providing non-periodical nanoholes to the film.

The invention is also of a method for extraordinary optical transmittance (EOT) through an optically thick metal film, comprising: providing the film with non-periodical nanoholes; and directing at the film light beams; thereby inducing EOT through the film.

The invention is further of an optical logic element operating according to either of the above methods. In the preferred embodiment, the element is an optical gate (preferably employing on/off switching of the control beams), optical switch, optical transistor, optical modulator (preferably by providing modulation of the control beams), or optical filter (preferably tunable by magnetic field and/or being controlled by light beams with different wavelengths).

The invention is still further of a method for enhancing signals in and sensitivity of a near-field scanning optical microscope (and such a microscope), comprising providing a metal film with non-periodical nanoholes and coating an optical probe of the microscope with the film.

The invention is yet further of a method for surface-enhanced spectroscopy and corresponding spectroscopic device, comprising: providing metal objects selected from the group consisting of nanowires, nanorods, and spheroids with thickness between approximately 1 nm to 500 nm and length between approximately 5 nm to 100 microns; and inducing light excitation of plasmon and plasmon polariton modes in the metal objects; thereby performing surface-enhanced spectroscopy of analyte molecules located proximate a surface of the metal objects. In the preferred embodiment, a metal-dielectric composite comprising the metal objects is employed, with a metal filing factor p in the composite ranging between 0.00001 and 0.99999.

The invention is additionally of method for surface-enhanced photochemistry and photobiology (and a corresponding device), comprising: providing metal objects selected from the group consisting of nanowires, nanorods, and spheroids with thickness between approximately 1 nm to 500 nm and length between approximately 5 nm to 100 microns; and inducing light excitation of plasmon and plasmon polariton modes in the metal objects; thereby performing surface-enhanced photochemistry and photobiology of molecules located proximate a surface of the metal objects.

The invention is also of a material with negative refractive index comprising metal objects which are nanowires, nanorods, or spheroids with thickness between approximately 1 nm to 500 nm and length between approximately 5 nm to 100 microns. In the preferred embodiment, the metal objects comprise at least one metal selected from silver, gold, copper, platinum, nickel, and aluminum. They are preferably combined into pairs with spacing between the objects in the pair larger than object thickness and smaller than object length. The pairs may be placed in a single layer, a multi-layer structure, or in a dielectric host. The material preferably has negative refraction in one or more spectral ranges selected from infrared, visible, and near ultra-violet, at light wavelengths between approximately 100 microns and 0.1 micron.

The invention is still further of an optical device comprising the above material. The device may comprise an optical lens comprising the material and may comprise integrated optical elements to control light at telecommunication wavelengths between approximately 1.3 microns to 1.6 microns.

The invention is also of a method of localizing, manipulating, guiding, and circuiting light (and optical device employing the method), comprising: providing chains of holes with sizes between approximately 1 nm to 9000 nm in a metal film; and directing at the metal film a light beam that excites one or more holes; thereby localizing, manipulating, guiding, and circuiting light along the holes in the film. In the preferred embodiment, the film has one or more elements from chains of hollows, chains of protrusions, chains of dielectric inclusions, and chains of semiconductor inclusions that are additionally excited. These are introduced to cause imitation of elements of conventional electronic circuits such as resistance elements, capacitance elements, and/or inductance elements. One or more of the holes and elements may comprise a nonlinear material, such as a photorefractive nanostructure. The invention operates to provide light circuiting and manipulation and control of photons in a manner analogous to manipulation and control of electrons in conventional electronic circuits. A device operating according to the method may comprise integrated optical elements to control light at telecommunications wavelengths between approximately 1.3 microns to 1.6 microns. A device operating according to the method may comprise one or more photonic chips comprising one or more photonic circuits.

The invention is further of a method for optical switching, comprising: providing chains of holes in a metal film, the holes having sizes between approximately 1 nm to 9000 nm, wherein the chains have shapes that allow light switching; directing at the metal film a light beam that excites one or more holes; and thereby switching optical light and controlling its propagation direction. In the preferred embodiment, the metal film comprises elements from chains of hollows, chains of protrusions, chains of dielectric inclusions, chains of semiconductor inclusions, and chains of nonlinear inclusions that may additionally be excited. One or more nonlinear inclusions may comprise a photorefractive nanostructure. An optical device operating according to the method may be, for example, an optical switch.

The invention is still further of a material comprising one or more metal films with chains of nanoholes having sizes between approximately 1 nm to 9000 nm and capable of operating as the metal film in either of the immediately preceding two methods. The films preferably comprise at least one metal selected from silver, gold, copper, platinum, nickel, and aluminum.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 17 illustrates a long needle modeled by chains of spheres according to the invention.

FIGS. 18(a)–(d) show EM field distribution for a long needle; the wavelength of incident light is 540 nm and the angle between the wavevector of incident light and the needle is 0° (a), 30° (b), 60° (c) and 90° (d).

DESCRIPTION OF THE PREFERRED EMBODIMENTS

BEST MODES FOR CARRYING OUT THE INVENTION

Figure 1:
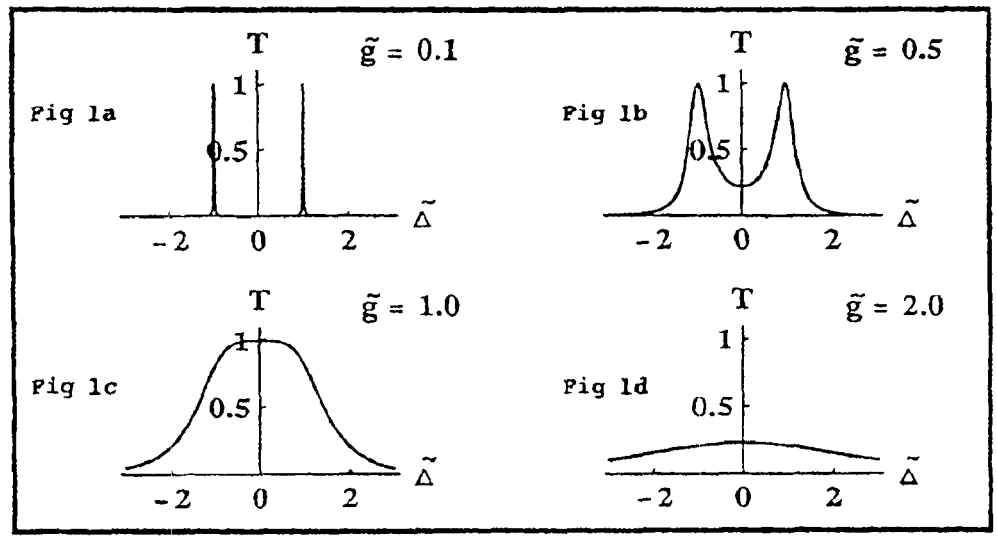
FIG. 1 illustrates resonance transmittance as a function of normalized detuning, $\Delta$, for different film modulations $\tilde{g}$.

The present invention is of apparatuses and methods employing extraordinary light transmittance through an optically thick metal film with (or without) subwavelength holes. The invention is also of apparatuses, materials, and methods employing metal nanowires for enhanced spectroscopy and left-handed materials.

When subwavelength holes are employed, film transmittance has sharp peaks that are due to the Maxwell-Garnet resonances in such holes. There are electric and magnetic resonances resulting in, respectively, dramatically enhanced electric and magnetic fields in the holes. An analytical expression for the resonance transmittance is stated that holds for arbitrary hole distribution in a device according to the invention. There are also other types of transmittance resonances in the case when the holes are arranged into a regular lattice. These resonances occur because of the excitation of surface plasmon polaritons propagating over the film surface. A combination of the two kinds of resonances results in a rich behavior of the extraordinary optical transmittance.

T. W. Ebbesen, et al., *Nature* 391, 667 (1998), show that light can experience extraordinarily large transmittance through subwavelength hole arrays in optically thick metal films. The effect of extraordinary transmittance is of great importance because it opens new ways to control photons with photons and makes possible a number of new applications, such as those of the present invention. Despite significant progress in numerical simulations of this interesting effect (e.g., by J. B. Pendry, et al., *Phys. Rev. Lett.* 86, 1114 (2001)) there has been an incomplete understanding of the enhanced transmittance. For example, Pendry, et al., do not explain long wavelength resonances (at light wavelengths significantly larger than the array period) observed in experiments by Ebbesen, et al.

A. K. Sarychev, et al., *Phys. Rev. B* 62, 8531 (2000) explains all the observed peaks in extraordinary transmittance. The short-wavelength peak is due to a new type of geometrical resonance (referred to as skin resonance because it occurs due to a strong skin effect); this resonance does not depend on periodicity and is of purely geometrical nature. The long-wavelength transmittance peaks, however, depend on periodicity and result from interactions of surface plasmons with the internal modes of the holes. For these modes, it is important that the EM field concentrates within the holes. In the course of propagation, the light is trapped by a hole for some time period, then it sneaks into the next hole where it is trapped again for some time, and so on. As a result, such surface electromagnetic mode propagates with the velocity, which is significantly smaller than light speed and therefore its wavelength is significantly smaller than the wavelength of the incident light. The slowing down of the light is the reason for the long-wavelength transmittance peaks observed experimentally. When the frequency of the incident wave is such that the wavelength of the sloweddown surface mode coincides with the period of the hole array, the corresponding surface mode is excited in the film. Since the metal film is optically thick, the mode is excited on the front interlace. Yet, being excited, it is spread over both sides of the plate since the surface modes on the two sides of the film, although weakly, yet are connected through the holes. There is close analogy between the surface waves on the two sides of the film and two coupled oscillators. The coupling can be arbitrary weak; still, if one pushes the first oscillator, then for the second oscillator it is only a matter of time to acquire roughly the same amplitude. Similarly, the amplitudes of the surface modes on the two sides of a thin metal plate eventually have approximately the same amplitudes. When the surface wave propagates on the backside of the film, it interacts with the holes and, as a result, the surface mode converts its energy back to the plane wave re-radiated by the film. Therefore, in resonance, the film becomes almost transparent regardless of its thickness. Note that the diameter of a hole does not play any role. It can be very small, yet the surface modes are excited and the film becomes transparent. Thus, the transmittance of an array of small holes in an optically thick metal film is of the resonant character, with the sharp peaks due to the excitation of a new type of surface waves resulting from the slowing down light in hole arrays.

Through optical nonlinearities of a film, optical transmittance can be controlled by the light itself, permitting creation of new devices such as optical gates, optical switches, and optical transistors. The surface modulation required for the excitation of plasmon polaritons on the two sides of the film and their coupling is created by light itself. Two control beams, which are incident on the surface at angles $\pm\Theta$ with respect to normal result in an interference pattern and thus in the modulation $\Delta n$ in the refractive index n for the fundamental beam propagating, for example, normal to the film. The modulation, in this case, can occur because of the Kerr optical nonlinearity that leads to correction $\Delta n = n_2 I$ for the refractive index $n = n_0 + n_2 I$. Similar to the array of holes that provide a small coupling between the polaritons on the two sides of the film, in this case, the periodic modulation $\Delta n$ may result in the coupling and thus in the extraordinary transmittance. As follows from the discussion above, the plasmon polaritons on the two sides of the film can be excited even at very small coupling (such as that provided by the subwavelength holes); therefore, the small modulation $\Delta n$ resulting from the Kerr optical nonlinearity can provide the desired result as well. In silver, for example, the optical nonlinearity responsible for the Kerr effect is rather large, $\chi^{(3)} \sim 10^{-8}$ e.s.u. Taking into account the local-field enhancement resulting from the excitation of surface plasmon polaritons, resonance transmittance modulation can be accomplished at the relatively low control beam intensity that can be achieved with available lasers.

To provide a modulation in the refractive index one can also use a thin layer of highly nonlinear material placed on top of the metal films. For example, photorefractive semiconductor quantum-well structures, D. D. Nolte, et al., "Photorefractive semiconductor nanostructures", *Handbook of Nanostructured Materials and Nanotechnology*, H. S. Nalwa, ed. (Academic Press, San Diego, 2000), which are known to produce a refractive index grating at very low intensities (below 1 mW) can be used for this purpose.

Note that n=n(I) determines the resonance frequency of plasmon polaritons. Such nonlinearity along with a feedback may result in a bistability phenomenon for the transmitted light, as described below. In this case, the light not only induces the resonance transmittance (by creating modulation in n) but also controls the magnitude of transmittance.

The present invention takes advantage of the recognition that extraordinary transmittance, first obtained for a periodic array of subwavelength holes, can also be obtained for arbitrary modulation in refractive index of the films (light-induced or fabricated). In other words, it can occur even with no holes at all. Also, if there is a "seed" modulation in the refractive index of a metal film (e.g., made by profiling or corrugating the metal surface), the transmittance can be further enhanced through the light-induced correction to the refractive index. In all cases, by employing the light-induced modulation in the refractive index, one can create and control the optical transmittance through optically thick metal film. This is a basic physical principle standing behind of the invention, which is based on control of photons with photons, as is done electronics, where electrons are controlled with electrons via the electric fields.

Photonic Nanocircuits. Arrays of holes in metal films can be used to guide and control photons, via excitation of plasmons, along the hole chains. Such holes can be arranged into any desired structures that can localize and guide the propagation of the electromagnetic energy along the structures as shown in FIG. 10. Such nanoengineered structures can be used as photonic devices and as integrated elements in optoelectronic devices, including most sophisticated ones, such as optical computers.

Figure 11:
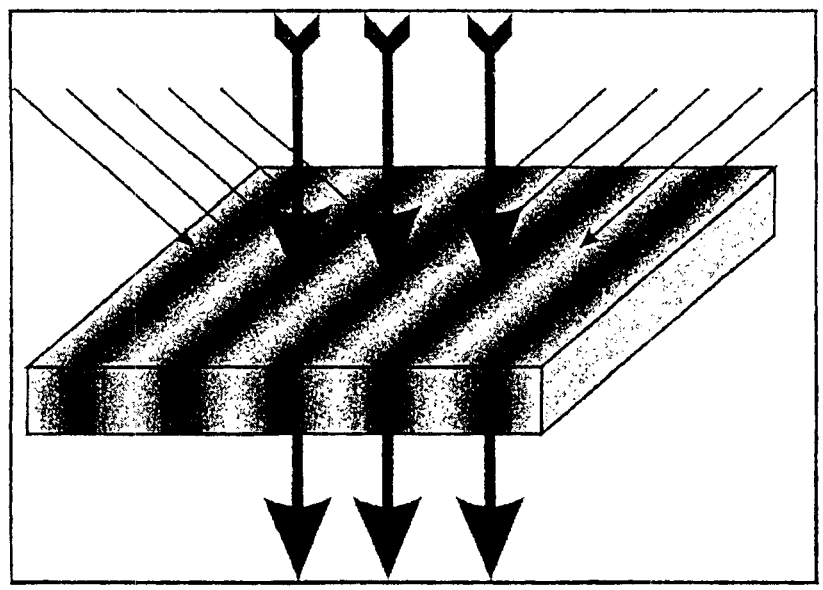
FIG. 11 is a schematic diagram of an Optical Gate based on the light-induced extraordinary optical transmittance of the invention (EOT).

Optical Gate. By switching on and off the two control beams, creating a modulation in the refractive index of the film, one can make the beam of interest (for simplicity, assume that it propagates normal to the film) be or not be transmitted through the film. Such an optical gate can operate very quickly, on the femtosecond or even shorter time scale; this is because for the control beams one can use ultra-short, femtosecond laser pulses. See FIG. 11.

Figure 12A:
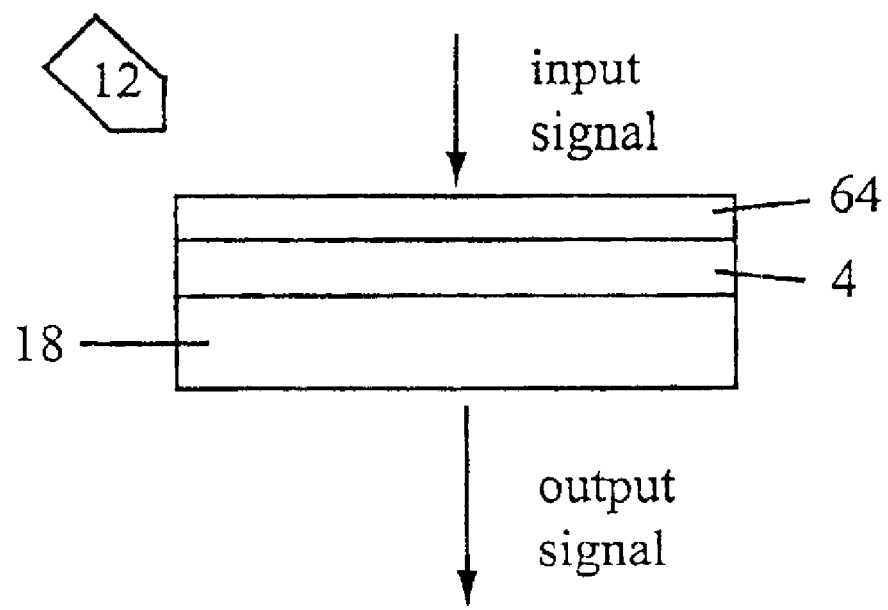
FIGS. 12(a)–(b) are schematic diagrams of an Optical Switch based on light-induced EOT, which may or may not have an additional coating layer of optical materials such as Kerr material or photorefractive layer; reference numerals are to light source 12, layer of optical material 64, metal film 4, and optional additional layer(s) for structural support and/or other purposes.
Figure 12B:
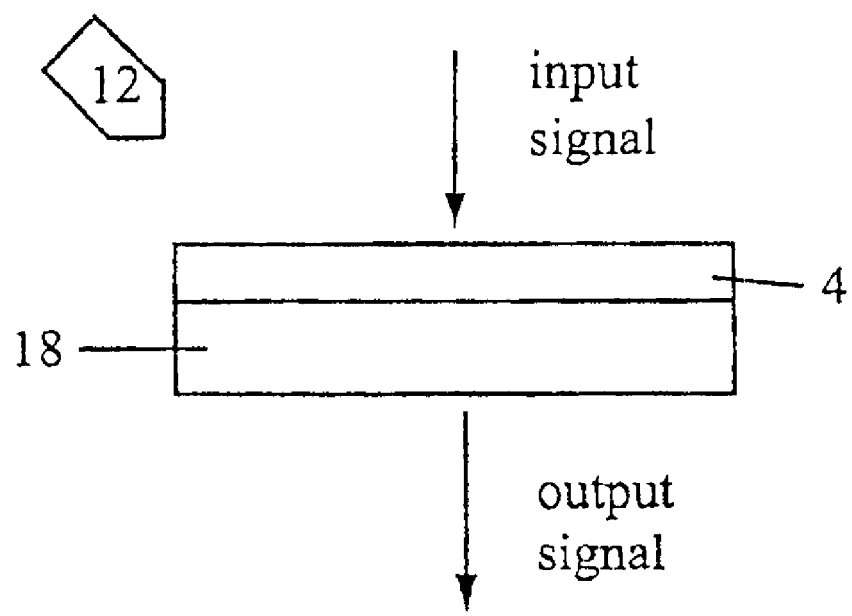

Optical Switch. By employing the bistable behavior of the transmittance, in this case by sending ultra-short laser pulses, one can switch the transmittance between its two stable states so that it will operate as an optical switch. The switch of the invention can be used to store binary information and thus also be used as an element of optical computer (e.g., random-access memory). See FIG. 12.

Figure 13:
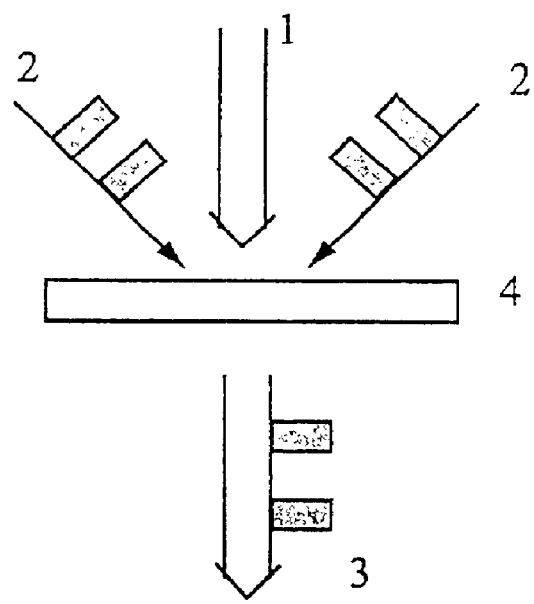
FIG. 13 is a schematic diagram of an Optical Transistor based on light-induced EOT; reference numerals are to input beam 1, control beams 2 bearing information and providing the light-induced EOT, output signal 3, and metal film 4.
Figure 14:
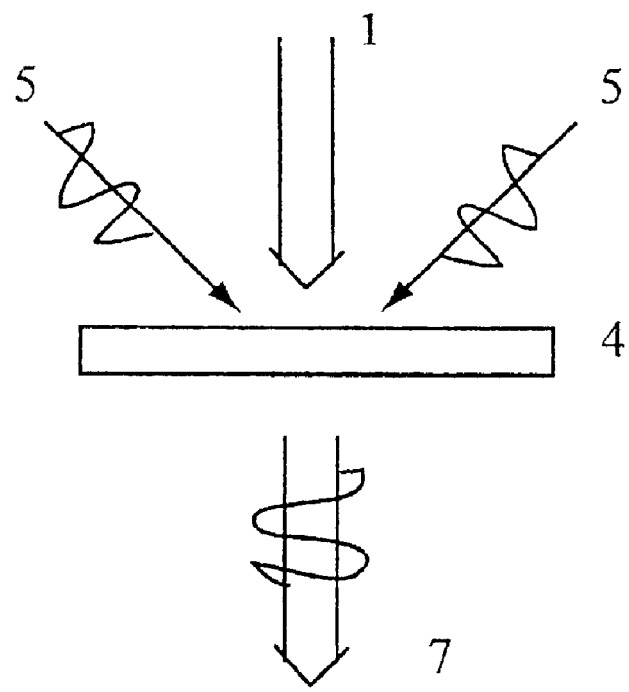
FIG. 14 is a schematic diagram of an Optical Modulator based on light-induced EOT; reference numerals are to input beam 1, modulated beams 5, output signal 7, and metal film 4.

All-Optical Transistor or Modulator. If the two control beams are modulated so that they bear information, they can be used for transferring this information into the strong beam that experiences the resonance transmittance. In this case, the extraordinary transmittance controlled by the control beams works as an all-optical transistor, which is an analog of a conventional transistor in electronics. See FIG. 13. Again, such optical transistor can operate very fast (much faster than its electronics counterpart). The same approach can he also used for making very fast optical modulators. See FIG. 14.

Figure 15:
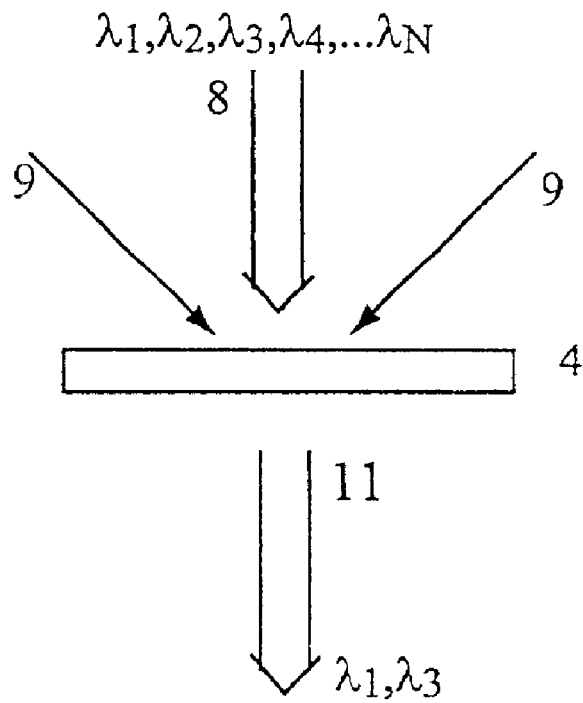
FIG. 15 is a schematic diagram of an Optical Filter based on light-induced EOT; reference numerals are to multi-wavelength input signal 8, control beams 9 inducing the EOT, metal film 4, and output beam 11 carrying only selected wavelengths.
Figure 16:
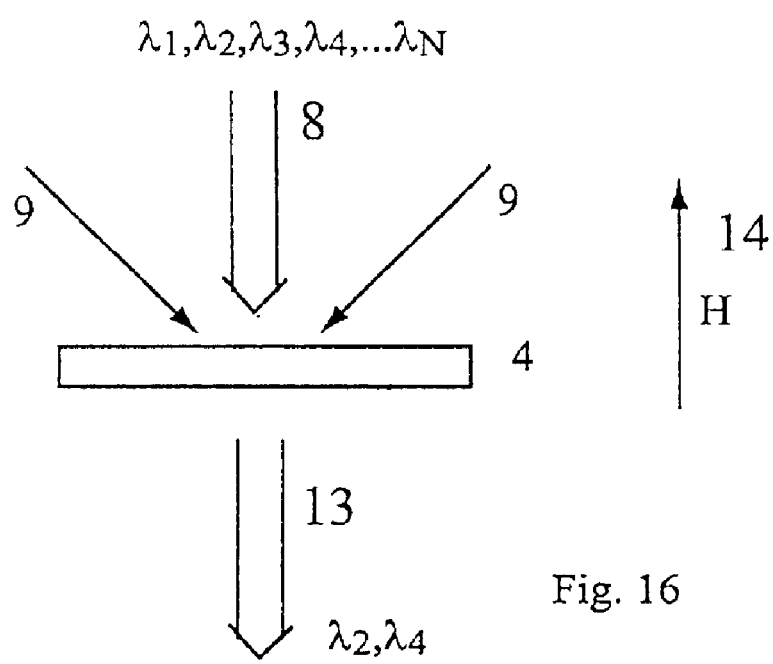
FIG. 16 is a schematic diagram of a tunable Optical Filter based on light-induced EOT; reference numerals are to multi-wavelength input signal 8, control beams 9 inducing the EOT, metal film 4, magnetic field 14 that tunes wavelengths to be transmitted through the film, and output signal 13 carrying the selected wavelengths.

Optical Filter. Because the resonant transmittance is concentrated in the spectral domain within very narrow sharp peaks, the light-managed transmittance can be used as an optical filter. See FIG. 15. Moreover, by controlling the spectral positions of the transmittance peaks (for example, with the magnetic fields that affect the plasmon polariton frequency) one can also make wavelength-tunable optical filters. See FIG. 16.

The devices according to the invention take advantage of the following physical principles:

Surface Plasmon Polaritons. The electromagnetic field coupled to free electrons in metals can result in plasmon polaritons propagating on the metal (see, e.g., L. D. Landau, et al., *Electrodynamics of Continuous Media*, 2d ed. (Pergamon, Oxford, 1984); and V. D. Freilikher, et al., *Phys. Rep.* 288, 127 (1997)). These surface waves can be excited when the real part of the metal permittivity, $\epsilon_m = \epsilon'_m + i\epsilon''_m$, is negative, i.e., $\epsilon'_m < 0$, and losses are relatively small $\kappa = \epsilon''_m / |\epsilon'_m| << 1$, which is typical for metals in the optical range. The real refractive index n is introduced below via the relation $\epsilon'_m = -n^2$.

At the metal-air interface, the surface plasmon polariton (SPP) is an H wave, with the direction of the magnetic field H parallel to the metal surface. Landau, et al., supra. In the direction perpendicular to the interface, SPPs exponentially decay in both media. The relation between frequency $\omega$ and wavevector $k_p$ of SPP can be found from the following consideration. Take the interface as the xy plane and assume that the SPP propagates in the x direction, with the field H being in the y direction: H={0,H,0}. For simplicity, assume that the x>0 half-space is vacuum, with dielectric constant $\in=1$, and neglect losses for metal in the z<0 half-space. Seek for solutions for the field in the following form:

$$H_0 = H_0 \exp(ik_p x - \Lambda_0 z), \Lambda_0 = \sqrt{k_p^2 - k^2} \text{ for } z>0$$

$$H_1 = H_0 \exp(ik_p x - \Lambda_1 z), \Lambda_1 = \sqrt{k_p^2 + (kn)^2} \text{ for } z<0 \quad (1)$$

where $k=\omega/c$ is the wavevector. Thus, the boundary condition requiring that H is continuous is satisfied; the continuity requirement for the electric field Ex, which is found from the Maxwell equation curl $H=-ik\in_m E$, results in the condition $$\frac{\partial H_0}{\partial z} = -\frac{1}{n^2}\frac{\partial H_1}{\partial z}, \quad (2)$$

for z=0. For n>1, this equation can be satisfied and it yields the following dispersion equation:

$$k_p = \frac{kn}{\sqrt{n^2 - 1}} \quad (3)$$

for the wavevector $k_p$ of SPP.

The component $E_z$ of the electric field in the SPP takes the following values on the metal interface: $E_z$ equals to $E_z(+0) = -(k_p/k)H_0 \exp(ik_p x)$ in the vacuum side of the interface and $E_z(-0) = -(k_p/n^2 k)H_0 \exp(ik_p x) \neq E_z(-0)$ in the opposite (metal) side. The discontinuity in the electric field is due the surface charge density $$\rho(x) = \frac{1}{4\pi}[E_z(+0) - E_z(-0)] = \frac{k_p(1+n^2)}{4\pi n^2 k}\exp(ik_p x), \quad (4)$$

which propagates together with the electric and magnetic fields along the interface.

Thus the SPP is a wave that consists of electromagnetic field and surface charges coupled together. Since SPP propagation includes rearrangement of the electron density, it not surprising that its speed $c_p=\omega/k_p-c\sqrt{n^2-1}/n$ is less than the speed of light c. As a result, the SPP cannot be excited by an external electromagnetic wave on a perfectly flat metal surface. When the refractive index n approaches 1 from above, that is, the metal dielectric constant $\in_m \to -1+0$, the SPP velocity $c_p$ vanishes so that the SPP "stops" on the metal surface.

In this case, the surface charge diverges as $(n^2-1)^{-1/2}$, as well as the normal component of the electric field. This phenomenon is known as a plasmon resonance in a metal plate. The SPPs can propagate not only on the metal surface but also on the surface of artificial electromagnetic crystals, for example, wire mesh crystals, D. F. Sievenpiper, et al., *Phys. Rev. Lett.* 76, 2480 (1996); J. B. Pendry, et al., *Phys. Rev. Lett.* 76, 4773 (1996); and Sarychev, et al., supra; this is because the real part of the effective dielectric constant can be negative in these metastructures.

There are two kinds of SPPs in the film of a finite thickness d, which correspond to symmetric and antisymmetric (with respect to the reflection in the film plane z=0) solutions to the Maxwell equations. Hereafter, we still use the "refraction index" defined as $n=\sqrt{\in_m}$ and neglect losses; it is also supposed that n>1. One is interested in the case of a strong skin effect when $\exp(-dkn)<<1$ so that the field decays exponentially in the film. Then the propagation of SPP is determined by the following equation:

$$k_{1,2} = k_p\left[1 \pm \frac{2n^2}{n^4-1}\exp(-dk_p n)\right] \quad (5)$$

where the wavevectors $k_1$ and $k_2$ correspond to symmetric and antisymmetric polaritons respectively, and $k_p$ is defined by Eq. (3). It is important that both symmetric and antisymmetric SPPs propagate on both sides of the film. Moreover, since both SPPs represent the eigenmodes of the film, the magnitudes of the electric and magnetic fields are the same on both interfaces. This consideration holds for arbitrarily thick film, although the difference between the two types of SPPs becomes exponentially smaller for the optically thick films $dk_p n>>1$. Velocities of symmetric and antisymmetric SPPs are both less than the light speed, and these SPPs cannot be excited by external electromagnetic waves because this would violate momentum conservation. In this sense, the SPPs represent a "hidden reality" that cannot be seen since it does not interact with light.

The situation changes dramatically when the film is periodically modulated. In this case the modulation provides the momentum needed to compensate for the difference in the photon and SPP momenta so that SPPs can be excited by an incident electromagnetic wave. An example of such spatial modulation is the square array of nano-holes punched in the film as in the experiments of Ebbesen, et al., supra; H. F. Ghaemi, et al., *Phys. Rev. B* 58, 6779 (1998); and T. J. Kim, et al., *Opt. Lett.* 24, 256 (1999).

Another example of a regular modulation of the refractive index, which is employed by the present invention, is the light-induced modulation in n occurring because of the optical Kerr (or other) nonlinearity; such n-modulation results from interference of two additional control laser beams which are incident on the surface from the different sides with respect to the normal. Suppose for simplicity that the electromagnetic wave of interest is incident normal to the film. Then the electromagnetic field in the film is spatially modulated with the period a because of the film inhomogeneity, specially fabricated or light-induced. When the frequency of an incident wave is such that SPP wavelengths $\lambda_{1,2}=2\pi/k_{1,2}$ ($k_{1,2}$ are given by Eq. (5)) coincide with the period of the modulation a, the SPPs are excited in the film. Since the film is optically thick the SPP is excited first on the front interface of the film. Yet eventually it spreads out on both sides of the film. There is a straightforward analogy between the front and backside SPPs and two identical oscillators coupled together. The coupling can be arbitrary weak, nevertheless, one pushes the first oscillator then, in some time (which depends on the coupling) the second oscillator starts to oscillate with the same amplitude as the first oscillator. By the same token, SPPs will have eventually the same amplitudes on the front and back interfaces. When SPP propagates on the back side of the film it interacts with the film modulation and, as a result, converts its energy back to the plane wave re-emitted from the film. Therefore, at the resonance, the film becomes almost transparent, regardless of its thickness; however, the width of the transmittance resonance shrinks when the film thickness d increases. Note that the amplitude $g \cong \Delta n/n$ of the film modulation does not play any role. The modulation g could be arbitrary small, yet the SPPs are excited and the film becomes transparent. Moreover, one does not need any holes for the resonance transmittance to occur. It is only needed that both sides of a metal film are modulated with the same spatial period. The minimum of the modulation needed for extraordinary transmittance depends on losses in metal, which can be relatively small (in particular, when the skin effect is strong). Note, that the transmittance maximum has typically a doublet structure corresponding to the excitation of symmetric and antisymmetric SPPS.

Resonance Transmittance Through Thin Films. A film modulation can always be expanded in Fourier series. The resonance transmittance takes place when frequency of the incident wave is such that one of the SPP wavevectors $k_{1,2}$ equals the wavevector q of a spatial harmonic. The resonance interaction of a SPP with the q-th spatial harmonic results in the enhanced transmittance. Since other spatial harmonics are out of the resonance and its amplitudes are small one can consider the interaction of the incident wave only with the resonant spatial mode. As mentioned, suppose that the magnetic field H in the incident wave has only y, component H={0, H,0} and consider the interaction of the incident wave with the metal film with the dielectric constant varying as $$\in_r = -n^2(1 + g \cos qx), \quad (6)$$

where the amplitude of the modulation is small, g<<1.

For a plane electromagnetic wave propagating normal to the film (along the z axis) the amplitude depends on z only. In the course of the interaction with the film modulation (6) the electromagnetic harmonic is generated which is proportional to cosqx. The amplitude of this harmonic is proportional to the film modulation g<<1. This harmonic, in turn, interacts with the film modulation and thus it is converted to the cos 2qx harmonic, etc. Thus, the whole spectrum of the electromagnetic waves is excited in the film when the incident plane wave interacts with the film modulation. The amplitudes of cos 2qx harmonics are proportional to $g^2$; the cos 3qx harmonics are proportional to $g^3$, etc. The resonance transmittance occurs when these harmonics are converted back to the plane wave transmitted through the film. One is interested in the electromagnetic harmonics that can be converted back to the plane wave in such a way that this optical process is proportional to the lowest power of the modulation g. Therefore one restricts consideration to cosqx harmonics and considers the magnetic field in the following form: $H_y(r,z) = H(z) + H_q(z) \cos qx$, where $H(z)$ and $H_q(z)$ are two unknown functions that determine the electromagnetic field inside and outside the film when the resonance transmittance occurs.

Substitute the field $H = \{0, H(z) + H_q(z) \cos qx, 0\}$ in the Maxwell equations and equate the terms that have the same dependence on the "x" coordinate. Lord B. Rayleigh, *The Theory of Sound*, 2d ed. (MacMillan, London, 1896). Then neglect the generation of higher harmonics and obtain the system of two differential equations:

$$H'' - (kn)^2 H - \frac{g}{2} H_q'' = 0, \quad (7)$$
$$H_q'' - [(kn)^2 + q^2] H_q - g H'' = 0$$

that determine the fields inside the film. The solution of these equations has the following form:

$$\begin{Bmatrix} H \\ H_q \end{Bmatrix} = A_1 [X_1 \sinh(\Lambda_1 knz) + X_2 \cosh(\Lambda_1 knz)] + A_2 [Y_2 \sinh(\Lambda_2 knz) + Y_2 \cosh(\Lambda_2 knz)], \quad (8)$$

where $$\Lambda_1 = \sqrt{\frac{2 - Q + q_1^2}{2 - g^2}}, \quad \Lambda_2 = \sqrt{\frac{2 + Q + q_1^2}{2 - g^2}}, \quad (9)$$

are dimensionless eigenvalues, and $$A_1 = \begin{Bmatrix} \frac{Q + q_1^2 - g^2(1 + q_1^2)}{(2 - g^2) q_1^2} \\ g \frac{2 - Q + q_1^2}{(2 - g^2) q_1^2} \end{Bmatrix}, \quad A_2 = \begin{Bmatrix} -g \frac{2 + Q + q_1^2}{2(2 - g^2) q_1^2} \\ \frac{g^2 + Q + q_1^2}{(2 - g^2) q_1^2} \end{Bmatrix}, \quad (10)$$

$$Q = \sqrt{q_1^4 + 2g^2(1 + q_1^2)}, \quad q_1 = \frac{q}{kn},$$

are eigenvectors of Eqs. (7). It follows from Eq. (8) that the field inside the film is determined by two pairs of constants, namely, $\{X_1, X_2\}$ and $\{Y_1, Y_2\}$.

For a smooth film, i.e., when the modulation g→0, the eigenvectors $A_1$ and $A_2$ acquire the values $A_1 = \{1,0\}$ and $A_2 = \{0,1\}$ Therefore, the constants $\{X_1, X_2\}$ correspond to the fundamental beam whereas the other two constants $\{Y_1, Y_2\}$ describe the q-th mode. The field in the reflected wave can be represented as $H(z) = \exp(ikz) + r \exp(-ikz)$, for $z < -d/2$, where r is the reflection coefficient. The field in the transmitted wave has the form $H(z) = t \exp(ikz)$, for $z > d/2$, where $T = |t|^2$ is the transmittance. For the q mode one uses the radiation boundary conditions, namely $H_q(Z) = Y_3 \exp(-i\sqrt{k^2 - q^2} z)$, for $z < -d/2$, and $H_q(z) = Y_4 \exp(i\sqrt{k^2 - q^2} z)$, for $z > d/2$, where $Y_3$ and $Y_4$ are constants. Note that at the resonance transmittance the wave vector k is less than the modulation vector q, which equals to one of the SPPs wavevectors, $k_{1,2} > k$, so that the field $H_q$ decays exponentially outside the film. Thus the electromagnetic field in the whole space is completely determined by two vectors $X = \{X_1, X_2, r, t\}$ and $Y = \{Y_1, Y_2, Y_3, Y_4\}$. Match the electric and magnetic fields inside and outside the film and obtain the following system of linear equations for the vectors X and Y:

$$\hat{H}X + g\hat{G}_1 Y = Z, \quad \hat{H}_q Y + g\hat{G}_2 X = 0 \quad (11)$$

where the vector Z is proportional to the amplitude of the incident wave, which is chosen to be equal to one, i.e., $Z = \{1,1,0,0\}$; while 4×4 matrixes H, $G_1$, and $G_2$, are given by the following formulae:

$$\hat{H} = \begin{Bmatrix} 1 & \tanh\left(\frac{dkn}{2}\right) & -1 & 0 \\ -\frac{i}{n}\tanh\left(\frac{dkn}{2}\right) & -\frac{i}{n} & 1 & 0 \\ 1 & -\tanh\left(\frac{dkn}{2}\right) & 0 & -1 \\ \frac{i}{n}\tanh\left(\frac{dkn}{2}\right) & -\frac{i}{n} & 0 & -1 \end{Bmatrix}, \quad (12)$$

$$\hat{G}_1 = g \begin{Bmatrix} -n^2/2 & -n^2/2 & 0 & 0 \\ im/2 & im/2 & 0 & 0 \\ -n^2/2 & n^2/2 & 0 & 0 \\ -im/2 & im/2 & 0 & 0 \end{Bmatrix}, \quad \hat{G}_2 = g \begin{Bmatrix} m^2 & m^2 & 0 & 0 \\ -in & -in & 0 & 0 \\ m^2 & m^2 & 0 & 0 \\ in & -in & 0 & 0 \end{Bmatrix}, \quad (13)$$

where $m = \sqrt{n^{2-}}$. The matrix $\hat{H}_q$, which appears in the second of Eqs. (11), has singular regular parts. Neglect the regular part of $H_q$ since it is proportional to $g^2$ and write the singular part in the following form:

$$\hat{H}_q^{-1} = \frac{1}{D_1} \begin{Bmatrix} -1 & im & -1 & -im \\ 0 & 0 & 0 & 0 \\ -1 & im & -1 & -im \\ -1 & im & -1 & -im \end{Bmatrix} + \frac{1}{D_2} \begin{Bmatrix} 0 & 0 & 0 & 0 \\ -1 & im & 1 & im \\ -1 & im & 1 & im \\ 1 & -im & -1 & -im \end{Bmatrix}, \quad (14)$$

where $$D_{1,2} = \frac{2m(1+n^2)\Delta}{n} \pm 4\varsigma - \frac{g^2 n^2}{2}, \quad (15)$$

where $\Delta(k)=k/q-m/n$, and $\zeta=\exp(-dnq)$. Note that in the derivation of Eqs. (12)–(15) one still supposes that $g \ll 1$, $\zeta \ll 1$, and the resonance transmittance occurs when $q \approx k_p = kn/m$.

The solution to Eqs. (11) can be written in the following form:

$$X=(\hat{H}-g^2\hat{G}_1\hat{H}_q^{-1}\hat{G}_2)Z. \quad (16)$$

When the modulation $g=0$, Eq. (16) reduces to $X=\hat{H}Z$ and gives the result for transmittance T of a uniform film $T=4n^2/[4n^2+(1+n^2)^2\sin h(dkn)^2]$ Although the second term in Eq. (16) $\propto g^2$, it cannot be neglected, even for $g \ll 1$, because $H_q$ is a singular matrix which can be very large at the resonance. The basic Eq. (16) can be easily solved analytically, and it gives the resonance transmittance through a modulated metal film. If one neglects nonresonant (direct) transmittance, i.e., one sets tanh $(2/dkn/)=1$ in Eq. (12), then one obtains a simple equation for the resonance transmittance:

$$T(\tilde{\Delta}) = \frac{4\tilde{g}^4}{\left[(\tilde{\Delta}-1)^2 + (\tilde{g}^2+\tilde{\kappa})^2\right]\left[(\tilde{\Delta}+1)^2 + (\tilde{g}^2+\tilde{\kappa})^2\right]} \quad (17)$$

that depends on the renormalized detuning from the SPP frequency, $$\tilde{\Delta} = g^2 \frac{n(n-m)^2(n+n^3+2m)}{8(1+n^2)\varsigma} - \frac{\Delta}{\varsigma} \frac{m(1+n^2)}{2n}, \quad (18)$$

renormalized modulation, $$\tilde{g} = \frac{gn\sqrt{m}(n-m)}{2\sqrt{1+n^2}\sqrt{\varsigma}}, \quad (19)$$

and losses in the system $$\tilde{\kappa} = \frac{(1+n^2)\kappa}{4n^2\varsigma}. \quad (20)$$

Recall that the metal dielectric constant $\in_m$ has been written in the form $\in_m = -n^2(1-i\kappa)$, where n is positive and larger than one.

To analyze the resonance transmittance, ignore, for simplicity, losses, i.e., set $\kappa=0$ in Eq. (17). Then, as follows from this equation, for modulation $\tilde{g}<1$, the resonance transmittance $T(\tilde{\Delta})$ has two maxima, as a function of $\tilde{\Delta}$, namely, $T(\tilde{\Delta}_1)=T(\tilde{\Delta}_2)=1$ for $\tilde{\Delta}_{1,2}=\pm 1-\tilde{g}^4$. Therefore, a lossless film becomes absolutely transparent at the resonance regardless of its thickness. It is instructive to consider how the transmittance changes when the modulation $\tilde{g}$ increases.

The distance between the two maxima, $\tilde{\Delta}_1-\tilde{\Delta}_2=21-\tilde{g}^4$, decreases with increasing amplitude $\tilde{g}$ of the modulation. The film remains transparent at the resonances. Finally when $\tilde{g}$ becomes larger than one, the two maxima merge together. Now the transmittance has one maximum, with amplitude $T_m=4\tilde{g}^4/(1+\tilde{g}^2)^2$ that decreases at further increase of $\tilde{g}$ (see FIG. 1).

As mentioned, the modulation can be made by punching a regular array of nano-holes. In this case the amplitude g is proportional to the hole radius squared, i.e., to $r^2$. Thus one obtains that the transmittance decreases when the hole radius increases. This result can be understood if one recalls that the interaction with the film's modulation results in the decay of SPP and its conversion to the emitted plane wave. The effective losses (term $\tilde{g}^2$ in the denominator of Eq. (17)) lead to the dumping of the SPP. As a result, the resonance transmittance increases with decreasing the modulation, i.e., with decreasing the hole radius.

Figure 2:
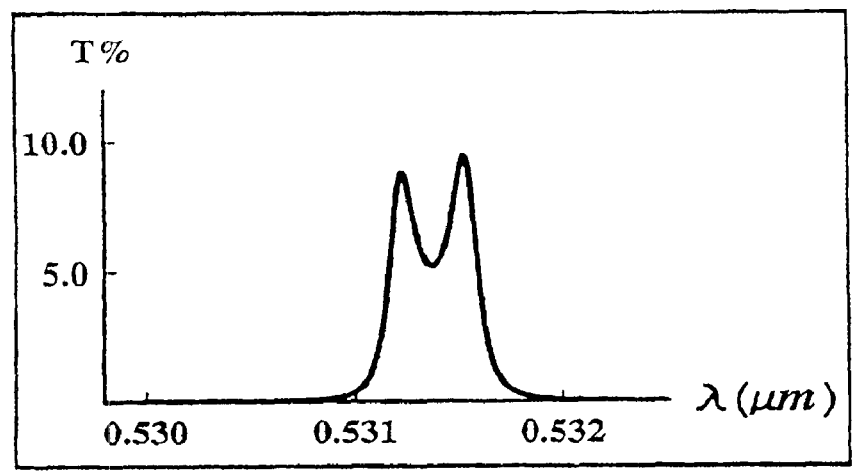
FIG. 2 illustrates transmittance of silver film at thickness d=0.18 $\mu$m and modulation amplitude g=0.1, with spatial period a=2Π/q=0.5 $\mu$m.

FIG. 2 shows results of calculations for the resonance transmittance for silver films, using a loss factor of $\kappa=1.6\times 10^{-3}$. As seen in the figure, the transmittance has sharp peaks corresponding to the SPP excitation, although the transmittance is less than 100% due to losses. By decreasing losses (for example, using low temperatures) one can further increase the transmittance. Arrays of holes can also provide a larger transmittance. Outside the resonance the transmittance is estimated as $T \sim \exp(-2nkd) \sim 10^{-6}$. Thus, at the resonance, the transmittance is enhanced by five orders of magnitude.

Figure 3:
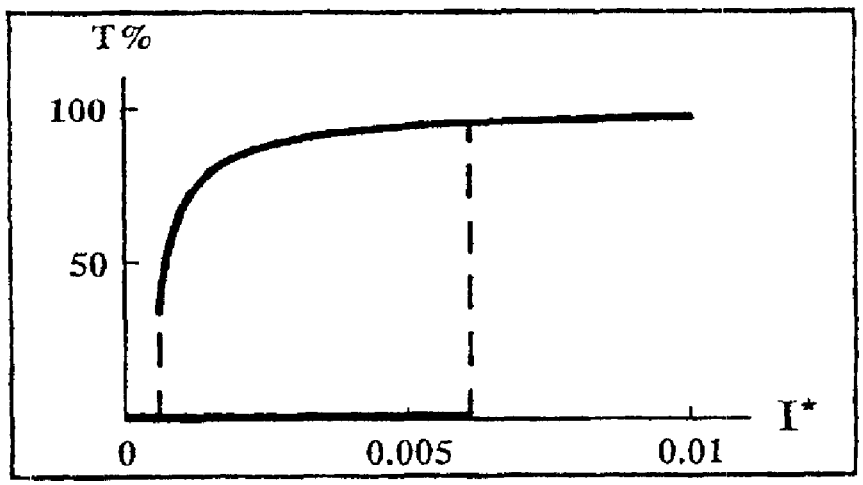
FIG. 3 is a graph of nonlinear transmittance as a function of the intensity $I_0$ of the incident light with $I^* = 24\pi^2 I_0 \chi^{(3)}/c$.

Light-Controlled Resonance Transmittance. In the section above, the film modulation was supposed to be somehow fabricated. Consider now the case when the film's modulation is created and controlled by light itself through the Kerr (or other) optical nonlinearity. First suppose that film has a "seed" modulation $g_0 \ll 1$ and consider how the modulation increases due to the nonlinearity of the film. Exactly at the resonance, the transmitted intensity $I_t=TI_0$ is of the same order of magnitude as the incident wave $I_0$. The transmitted wave is generated by SPP, which propagates on the back (output) interface (z=d/2) because of the SPP interaction with the film modulation g. Therefore, the amplitude of the SPP $I_p$ is estimated as $I_p \sim I_t/g^2 \sim I_0/g^2 \gg I_0$. At the front (input) interface (z=-d/2) the SPP amplitude is of the same order of magnitude. The electric field $E_p$ of the SPP is spatiality modulated with the resonance wavevector $k_p$. This field-induced modulation g, which is estimated as $g \sim 12\pi\chi^{(3)}|E_p|^2$, where $\chi^{(3)}$ is the Kerr nonlinear susceptibility. The induced modulation increases transmittance and, therefore, the amplitude of the SPP. This positive feedback may result in the bistability as shown in FIG. 3.

When intensify $I_0$ of the incident wave becomes larger than some $I_1$, the transmittance jumps from nearly zero up to $T \cong 1$, i.e., the film suddenly becomes transparent. If one decreases the intensify of the incident wave the film remains transparent, even for $I_c < I_1$ since the SPP has been already excited in the film. The transmittance decreases steeply for $I_0 \sim I_2 < I_1$. Thus, optical bistability can occur in modulated metal films. Note that the susceptibility $\chi^{(3)}$ is rather large for noble metals, $\chi^{(3)} > 10^{-8}$ e.s.u. (see S. Debrus, et al., *J. Appl. Phys.* 88, 4469 (2000) and P. J. Bennett, et al., *Opt. Lett* 24, 1373 (1999)) and the intensity $I_0$ required for the bistability can be easily achieved with conventional lasers. Also note that the seed modulation $g_0$ can also he created by two interfering laser beams. Note that by coating a metal film with a layer of a photorefractive quantum well structure (which has a very strong nonlinearity) the intensity needed for light-induced optical transmittance can be dramatically reduced.

To summarize, it has been shown herein that the excitation of the SPPs in modulated metal films can result in resonance transmittance so that an optically thick film can become transparent. The transmittance can be increased by a factor of $10^5$ and more at the resonance. The resonance transmittance occurs when the spatial period of the film modulation equals the wavelength of the SPP. The maximum in the transmittance has a characteristic double-peak structure due to the split of SPPs into symmetric and antisymmetric modes. The resonance transmittance increases with decreasing losses in the system, which can be achieved by cooling the film to cryogenic temperatures. Exactly at the resonance, the amplitude of the SPP can be orders of magnitude larger than the amplitude of the incident wave. The optical nonlinearity can result in significant enhancement of the discussed effect. At sufficiently large intensities of the incident wave the film manifests the desired optical bistability. As mentioned above, the films with such bistable behavior in the resonance transmittance can be used, for example, as optical switches or other optical devices. Most importantly, the resonance transmittance can be induced and controlled by light itself, which makes possible a number of applications heretofore unknown.

Use of Subwavelength Holes. For electromagnetic waves propagating on the surface of a metal film, in the optical and infrared spectral ranges, the excitation of the electron density coupled to the electromagnetic field results in SPP traveling on the metal surface (see e.g., Freilikher, et al., supra, and Landau, et al., supra). The SPPs can be excited when the real part of the metal permittivity $\in_m = \in'_m + i\in''_m$, is negative, $\in'_m < 0$, and losses are relatively small, $\kappa = \in''_m / |\in'_m| <<< 1$, which is typical for metals in the optical and infrared ranges. The negative metal permittivity $\in_m$ is denoted as $-n^2$.

At the metal-air interface, the SPP is an H wave, with the direction of the magnetic field H parallel to the metal surface. Landau, et al., supra. In the direction perpendicular to the interface, SPPs exponentially decay in both media. The SPPs can propagate not only on the metal surface but also on the surface of artificial electromagnetic crystals, for example, wire mesh crystals, Sievenpiper, et al., supra; Pendry, et al., supra; Sarychev, et al., supra; and A. K. Sarychev, et al., *Phys. Rep.* 335, 275 (2000); this is because the real part of the effective dielectric constant can be negative in these mesastructures.

Since the SPP propagation includes rearrangement of the electron density, it is not surprising that its speed $c_p = \omega/k_p$, $k_p = kn/\sqrt{n^{2-1}}$ is less than the speed of light c, where $k_p$ is wavevector of SPP and $k = \omega/c$. As a result, the SPP cannot be excited by an external electromagnetic wave on a perfectly flat metal surface. The situation, however, changes when the film is modulated. In this case, the EM field inside the film is also modulated. When one of the spatial periods of the modulation coincides with the wavelength of SPP, the latter can be excited by an incident EM wave.

Considering the surface electromagnetic waves and extraordinary light transmittance in optically thick metal films that are perforated with subwavelength holes, the transmittance has sharp resonances corresponding to the excitation of various surface waves. Some of these waves are similar to the SPP while others are localized surface waves that are specific for a perforated metal and were heretofore unknown. To reiterate, the extraordinary optical transmittance (EOT) was first discovered in the seminal work of Ebbesen, et al., supra, and then was intensively investigated (see, for example, Ghaemi, et al., supra; Kim, et al., supra; D. E. Grupp, et al., *Appl. Phys. Lett.* 77, 1569 (2000); C. Sonnichsen, et al., *Appl. Phys. Lett.* 76, 140 (2000); and A. Doganu, et al., *Opt. Lett.* 26, 450 (2001)). A number of various models (with most of them being numerical simulations) were suggested to explain the EOT. W. C. Tan, et al., *Phys. Rev. B* 59, 12661 (1999); W. C. Tan, et al., *Phys. Rev. B* 62, 11134 (2000); V. A. Shubin, at al., *Phys. Rev. B* 62, 11230 (2000) J. B. Pendry, et al., *Phys. Rev. Lett.* 86, 1114 (2001); L. Salomon, et al., *Phys. Rev. Lett.* 86, 1110(2001); and R. Wannemacher, *Opt. Comm.* 195, 107 (2001). Despite the very sophisticated simulation codes used, the physical picture of the EOT remained unclear. The present invention employs and takes advantage of an analytical approach referred to herein as the generalized Ohms' law (GOL). This approach allows development of a physical model, which provides both qualitative and quantitative pictures for the field distributions and EOT through a metal film with subwavelength holes.

The following discussion proceeds as follows. First, the GOL approximation is described and extended to the case of thick metal films. Then results for the local EM fields and effective parameters of the film are presented. Finally consideration is made of excitation SPPs on the film and comparison with experimental results.

GOL Approximation. An approach to the calculation of optical properties of metal dielectric films proposed and employed by, A. K. Sarychev, et al., *Phys. Rep.* 335, 275 (2000); Shubin, et al., supra; A. K. Sarychev, et al., *Physica A* 207, 372 (1994); A. K. Sarychev, et al., *Phys. Rev. B* 51, 5366 (1995); Levy-Nathansohn, et al., *Physica A* 241, 166 (1997); *Phys. Rev. B* 55, 5425 (1997); and A. N. Lagarkov, et al., *Physica A* 241, 199 (1997), is based on the full set of the Maxwell equations. This approach does not use the quasistatic approximation because the fields are not assumed to be curl-free inside the film. Although that theory was originally proposed for metal-insulator thin films, it is, in fact, quite general and can, under appropriate conditions, be applied to any kind of inhomogeneous film.

At the beginning, one restricts to the case where all the external fields are parallel to the plane of the film. This means that an incident wave, as well as reflected and transmitted waves, all propagate in the direction perpendicular to the film plane (excitation of the surface plasmons will be considered later). Focus consideration on the electric and magnetic field magnitudes at certain distances away from the film and relate them to the currents inside the film.

The boundary conditions completely determine solutions to the Maxwell equations for the fields inside a particular region of the film at the fixed frequency. Therefore the internal fields, which change very rapidly with position in the direction perpendicular to the film, depend linearly on the electric and magnetic field away from the film. The currents inside the film are linear functions of the local internal fields, which are determined by the usual local constitutive equations. Therefore, the currents flowing inside the film also depend linearly on the electric and magnetic fields outside the film. However, the electric current averaged over the film thickness now depends not only on the external electric field, but also on the external magnetic field. The same is true for the average magnetic induction current. Thus one has two linear equations that connect the two types of the average internal currents and the external fields. These equations can be considered as the generalization of the Ohm's law to the non-quasistatic case. The GOL forms the basis of a novel approach to calculating the electromagnetic properties of inhomogeneous films.

Figure 4A:
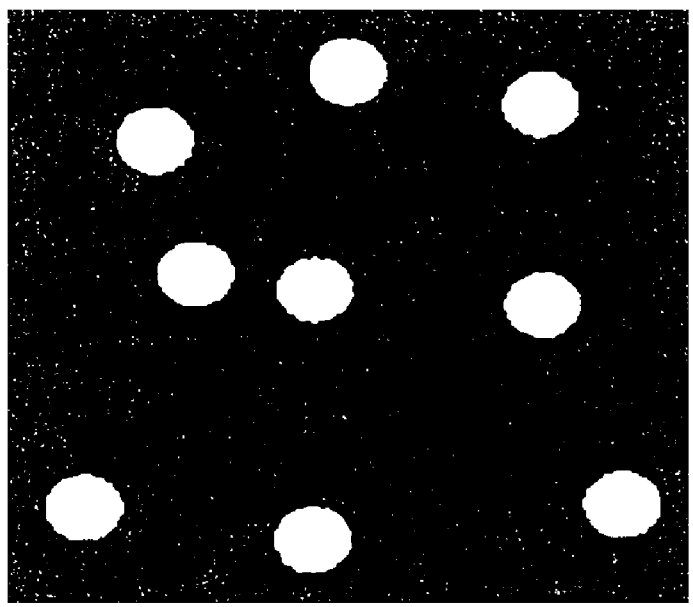
FIG. 4 illustrates aperiodic holes an optically thick metal film.
Figure 4B:
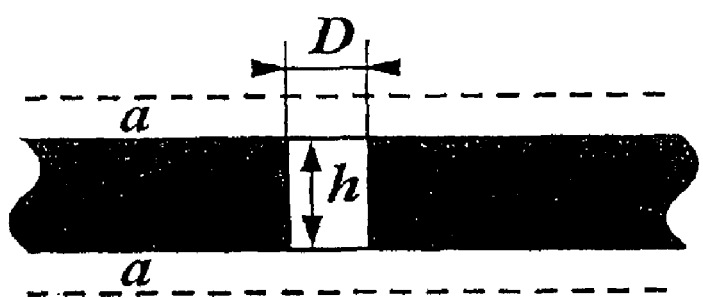

In actual calculations it is supposed that a metal film, with possible holes, voids, and other inhomogeneities, is placed in the xy plane so that the z axis is perpendicular to the film, which has thickness h. The external electromagnetic wave is incident onto the z=−h/2 interface of the film (back interface) and the transmitted wave is emitted from the z=h/2 interface (front interface). Typical spatial scale D of the film defects is supposed to be much smaller than the wavelength $\lambda$, i.e., D<<$\lambda$. For cylinder holes, D is the cylinder diameter (see FIG. 4 for illustration).

It is instructive to consider first the electric and magnetic fields on both sides of the film. Shubin, et al., supra; Levy-Nathansohn, et al., supra; and Lagarkov, et al., supra. Namely, the electric and magnetic fields are considered at the distance a behind the film $E_1(r)=E(r,-h/2-a)$, $H_1(r)=H(r,-h/2-a)$, and at the distance a in front of the film $E_2(r)=E(r,h/2+a)$, $H_2(r)=H(r,h/2+a)$. All the fields and currents considered are monochromatic fields, with the usual exp($-i\omega t$) time dependence. The vector r={x,y} in the above equations is a two-dimensional vector in the xy plane. In the case of laterally inhomogeneous films, the average electric displacement $$D(r) = \int_{-h-a}^{h+a} D(r,z) dz$$

and the average magnetic induction $$B(r) = \int_{-h-a}^{h+a} B(r,z) dz$$

are functions of vector r. In the GOL approximation it is supposed that the local electromagnetic field is a superposition of two plane waves propagating in +z and −z directions. This superposition of two waves is, indeed, different in different regions of the film. It is assumed below that electric field E(r,z) has a non-zero x component, E(r,z)={E(r,z),0,0}, and that magnetic field H(r,z), has a non-zero y component H(r,z)={0,H(r,z),0}. Consider for simplicity films that are locally isotropic so that the electric displacement D(r,z)={D(r,z),0,0} and magnetic induction B(r,z)={0,B(r,z),0} have the same polarization as electric and magnetic fields. Then the integration of the Maxwell equations curl E(r,z)=ikB(r,z) and curl H(r,z)=−ikD(r,z) over coordinate z between the planes z=−h/2−a and z=h/2+a gives the following result:

$$E_2(r)-E_1(r)=ikB(r),\ H_2(r)-H_1(r)=ikD(r), \quad (21)$$

where $H_1(r)=H(r,z=-h/2-a)$ and $E_1(r)=E(r,z=-h/2-a)$ are fields at the back interface, whereas $H_2(r)=H(r,z=h/2+a)$ and $E_2(r)=E(r,z=h/2+a)$ are front interface fields. In the GOL approximation the electric displacement D(r) is a linear function of the electric fields $E_1(r)$ and $E_2(r)$, as follows from the presentation of the local field by a superposition of two plane waves. Consider for simplicity films having the mirror symmetry with respect to reflection in the z=0 plane. For such films, the displacement D(r) is a symmetric function of the fields $E_1(r)$ and $E_2(r)$. Therefore, one can write that $kD(r)=u(r)[E_1(r)+E_2(r)]$, where u(r) is a dimensionless "Ohmic" parameter. A similar equation holds for the magnetic induction $kB(r)=v(r)[H_1(r)+H_2(r)]$, where v(r) is another dimensionless "Ohmic" parameter. Note that when the film thickness h is much smaller than the skin depth t, the Ohmic parameters u and v have the meaning of metal dielectric permittivity $\epsilon_m$ and magnetic permeability $\mu_m$, respectively; specifically, they are given by $u=k\epsilon_m$ and $v=k\mu_m$, in the "thin-film" limit.

The optical properties of the film, such as transmittance and reflectance, can be expressed in terms of the parameters u and v. To find the relations needed, substitute the equations for kD(r) and kB(r) in the Maxwell Eqs. (21) and then average them over the film plane. Thus one obtains:

$$<E_2>-<E_1>=ik<B>=iv_e(<H_1>+<H_2>), \quad (22)$$

$$<H_2>-<H_1>=ik<D>=iu_e(>E_1>+<E_2>), \quad (23)$$

where < ... > denotes the average over x,y coordinates. Above were introduced the effective film parameters, $u_e$ and $v_e$ through the relations:

$$u_e(<E_1>+<E_2>)=<u(E_1+E_2)>,\ v_e(<H_1>+<H_2>)=<v(H_1+H_2)>. \quad (24)$$

Eqs. (24) have the form typical for a constitutive equation in electrodynamics, but they include parameters u and v that depend on the local geometry of the film. These equations are referred to as the generalized Ohms' law (GOL).

Maxwell Eqs. (22) and (23) relate the average fields from both sides of the film and, therefore, allow one to find the transmittance, reflectance, etc. Suppose that the wave enters the film from z<0, so that its amplitude is proportional to $e^{ikz}$. The incident wave is partially reflected and partially transmitted through the film. The electric field amplitude in the z<0 half space, away from the film, can be written as $\tilde{E}_1(z)=e^{ikz}+re^{-ikz}$, where r is the reflection amplitude. Well behind the film, the electric component of the electromagnetic wave acquires the form $\tilde{E}_2(z)=te^{ikz}$, where t is the transmission amplitude. In the planes z=−h/2−a and z=h/2+a, the average electric field equals to <$E_1$> and <$E_2$>, respectively. The electric field in the wave is matched with the average fields in the planes z=−h/2−a and z=h/2+a, i.e., <$E_1$>=$\tilde{E}_1(z)(-h/2-a)=e^{-ik(h/2+a)}+re^{ik(h/2+a)}$ and <$E_2$>=$\tilde{E}_2(z)(h/2+a)=te^{ik(h/2+a)}$. The same matching with the magnetic fields gives <H>=$e^{-ik(h/2+a)}-re^{ik(h/2+a)}$ and <$H_2$>=$te^{ik(h/2+a)}$ in the planes z=−h/2−a and z=h/2+a respectively. The substitution of these expressions for the fields <$E_1$>,<$E_2$>, <$H_1$>, and <$H_2$> in Eqs. (22) and (23) gives two linear equations for t and r. By solving these equations, one obtains the reflectance and transmittance in the following form:

$$R \equiv |r|^2 = \left|\frac{(u_e-v_e)}{(i+u_e)(i+v_e)}\right|^2,\quad T \equiv |t|^2 = \left|\frac{1+u_ev_e}{(i+u_e)(i+v_e)}\right|^2. \quad (25)$$

Thus, the effective Ohmic parameters $u_e$ and $v_e$ completely determine the optical properties of inhomogeneous films. To find the effective parameters from the GOL Eq. (24), a number of efficient analytical and numerical methods, which were developed, for example, in the percolation model known in the art (see, e.g., A. K. Sarychev, et al., *Phys. Rep.* 335, 275 (2000)), can be used.

Transmittance of Nano-Holes. Now apply the above to find the transmittance of a metal film with subwavelength holes. To determine the effective parameters, use the Maxwell-Garnett (MG) approach, which can easily be generalized to a non-quasistatic case (see, e.g., A. K. Sarychev, et al., *Phys. Rep.* 335, 275 (2000)). Thus for the effective parameter, one obtains the following expression:

$$u_e \equiv \frac{\langle uE \rangle}{\langle E \rangle} = \frac{(1-p)u_mE_m + pu_hE_h}{(1-p)E_m + pE_h}, \quad (26)$$

where the surface hole concentration p is supposed to be small, p<<1, the coefficients $u_m$ and $u_h$, are the Ohmic parameters for the metal and holes, and the quantities $E_m=(E_1+E_2)_m$ and $E_h=(E_1+E_2)h$ are the electric fields averaged over the metal and holes, respectively. In the MG approach, one can use the dipole approximation that leads to the following expression:

$$E_h = \frac{2E_m u_m}{u_m + u_h}. \tag{27}$$

With the relation of Eq. (17) one can find $u_e$ from Eq. (26). Repeating the same procedure one can find the "magnetic" effective parameter $v_e$, which is expressed in terms of $v_m$ and $v_h$.

Now one substitutes the parameters $u_e$ and $v_e$ in Eq. (25) and obtains the following expression for the transmittance amplitude:

$$t = -\frac{4e^{-i(2a+h)k} p u_m^2 (1 + u_h v_h)}{\Sigma_1 \Sigma_2}, \tag{28}$$

$$\Sigma_1 = u_h - p u_h + (1+p)(1-iu_h)u_m - i(1-p)u_m^2, \tag{29}$$

$$\Sigma_2 = (i + u_m)(u_m v_h - 1) + p(i - u_m)(u_m v_h + 1), \tag{30}$$

where the relation $u_m = -1/v_m$ is used that holds when the metal skin depth $\delta$ is much smaller than the film thickness, $\delta \ll h$.

As follows from Eq. (27), the electric field in the hole can go to infinity at $u_m \to -u_h$. By substituting the $u_m \to -u_h$ in Eq. (28), one obtains the following expression for the resonance transmittance amplitude:

$$t_u = -\frac{2i e^{-i(2a+h)k} u_m}{1 + u_m^2}, \tag{31}$$

which does not depend on the hole concentration p and, therefore, remains finite, even for p→0.

When the magnetic resonance takes place, i.e., $v_m = -1/u_m = -v_h$, the resonance transmittance amplitude becomes $$t_v = \frac{2i e^{-i(2a+h)k} u_m}{1 + u_m^2}, \tag{32}$$

which also remains finite at p→0. Thus one obtains that the extraordinary optical transmittance is simply a result of electric and magnetic MG resonances in the holes.

For calculations of the transmittance, one finds the Ohmic parameters $u_m$, $u_h$, $v_m$, and $v_h$. Parameters $u_m$ and $v_m$ one can obtain directly from solutions to the Maxwell equations in the GOL approximation $u_m = -\cot(ak)$, $v_m = \tan(ak)$ so that $u_m = -1/v_m$ indeed. See A. K. Sarychev, et al., *Phys. Rev. B* 62, 8531 (2000). To get the hole parameters $u_h$ and $v_h$ one has to know the EM field distribution inside a hole. The inside field is a superposition of different eigenmodes for this subcritical wave guide. At the edge of the hole, the internal field is similar to the incident plane wave. When one goes deeper inside the hole, the mode with the smallest eigenvalue survives only. To simplify further qualitative consideration, assume that the internal field is a plane wave near the edges and it matches with the basic internal mode at the distance a from each end of the hole. As a result of such matching, one obtains $$u_d = \frac{k \tan(2ak) - \sqrt{\kappa^2 - k^2} \tanh\left[\left(\frac{h}{2} - a\right)\sqrt{\kappa^2 - k^2}\right]}{k + \sqrt{\kappa^2 - k^2} \tan(2ak)\tanh\left[\left(\frac{h}{2} - a\right)\sqrt{\kappa^2 - k^2}\right]}, \tag{33}$$

and $$v_d = \frac{\sqrt{\kappa^2 - k^2} \tan(2ak) + k\tanh\left[\left(\frac{h}{2} - a\right)\sqrt{\kappa^2 - k^2}\right]}{\sqrt{\kappa^2 - k^2} - k\tan(2ak)\tanh\left[\left(\frac{h}{2} - a\right)\sqrt{\kappa^2 - k^2}\right]}, \tag{34}$$

where $\kappa = 1.84/(2D)$ is the eigenvalue for the basic mode in a cylindrical wave guide, and D is the diameter of the hole. Note that the hole represents a subcritical wave guide, when 2 kD<1.84. Landau, et al., supra.

If holes are "shallow" enough so that h<2a, the wave remains almost planar inside the hole and the Ohmic parameters can be simplified to $u_h = v_h = \tan[(a+h/2)k]$. By substituting these expressions in Eq. (28) and considering the limit p<<1, one obtains the following expression for the transmittance:

$$T_r = \sum_j \frac{4p^2 \sin^4\left(\frac{2aj\pi}{4a+h}\right)}{4p^2 \sin^4\left(\frac{2aj\pi}{4a+h}\right) + (4a+h)^2\left(k - \frac{j\pi}{4a+h} + \frac{p}{4a+h}\sin\left(\frac{4aj\pi}{4a+h}\right)\right)^2}. \tag{35}$$

Figure 5:
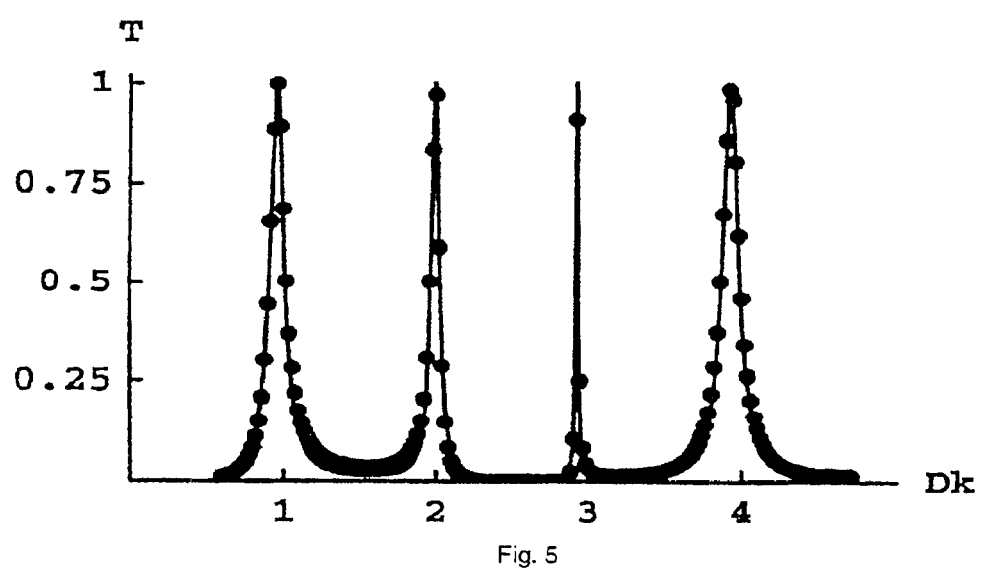
FIG. 5 is a graph of transmittance through shallow holes (h<2a); a/D=0.6, h/D=0.8, p=0.1; continuous line is by resonance approximation (Eq. (35)), points line calculated by Eq. (28).
Figure 6A:
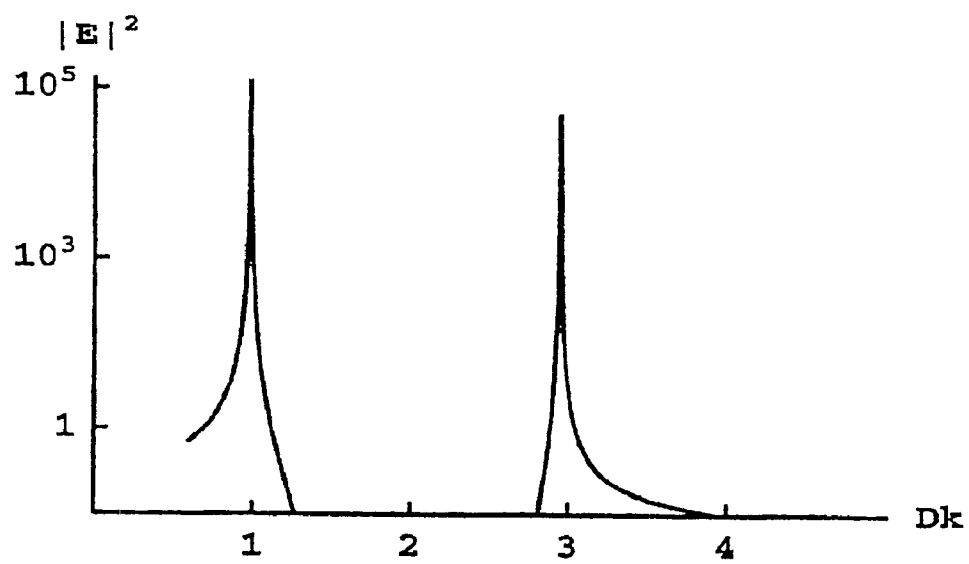
FIGS. 6($a$) and ($b$) show electric ($a$) and magnetic ($b$) field in a hole for the system of FIG. 5; field in the incident wave is taken as a unit.
Figure 6B:
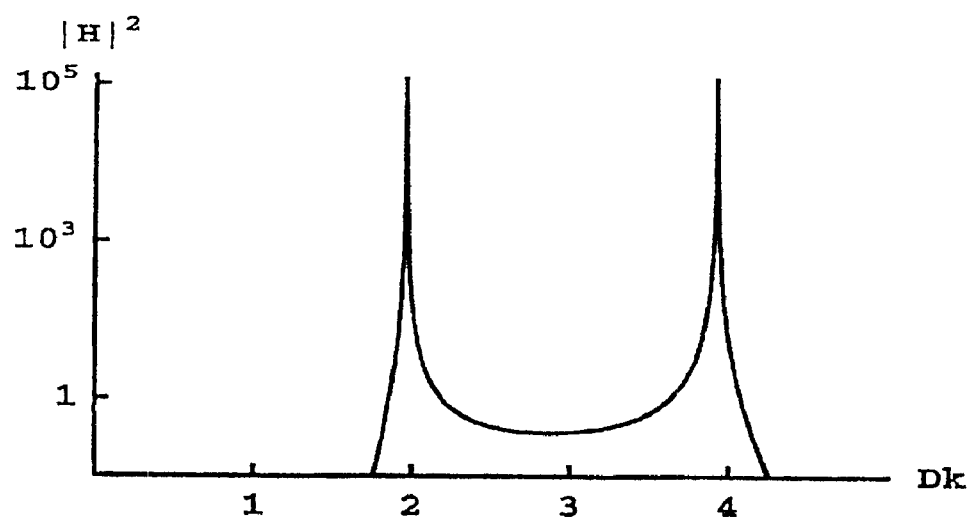
Figure 7A:
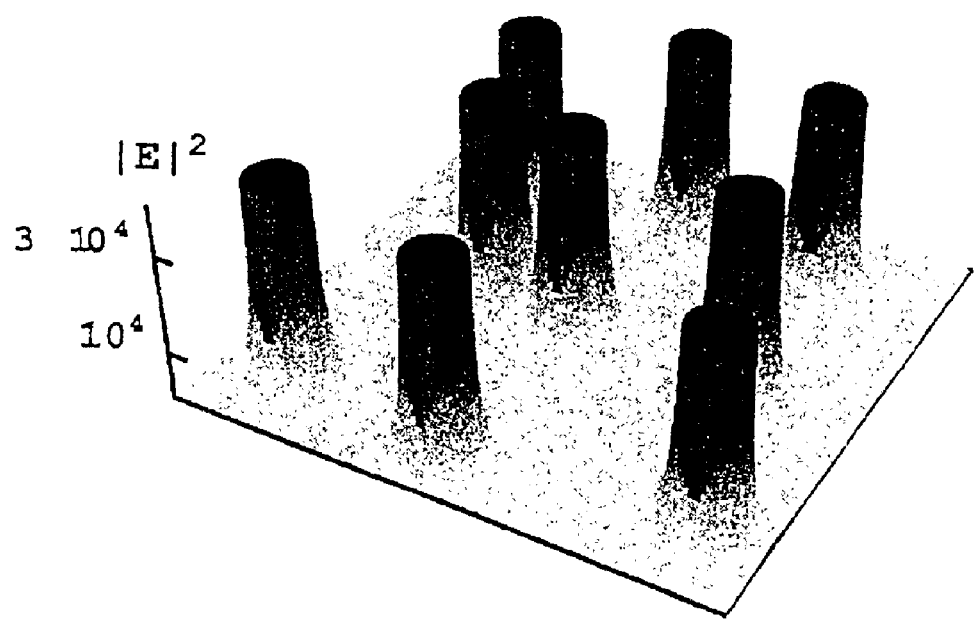
FIGS. 7($a$) and ($b$) show spatial distribution of electric ($a$) and magnetic ($b$) fields near MG resonance for the system in FIG. 5; ($a$) kD=0.992, ($b$) kD=1.96.
Figure 7B:
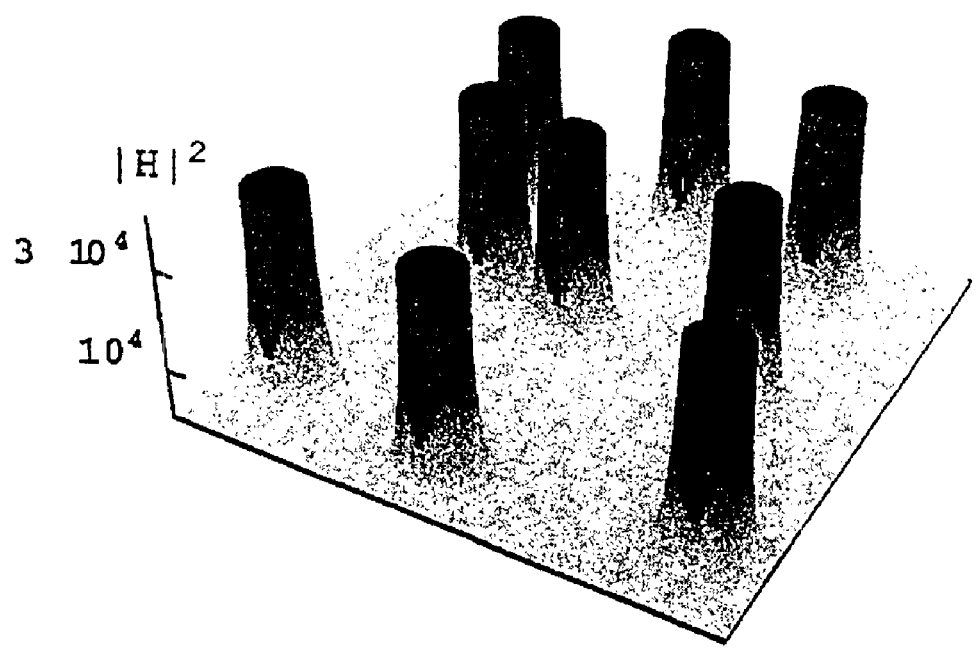

The thus obtained transmittance is shown in FIG. 5. The maximum position for T is a periodical function of k; the peak width depends on k. Some maxima can disappear when the corresponding numerators in Eq. (35) vanish. The odd resonances in Eq. (35) correspond to the maximum in the electric field in the holes, whereas the even resonances are due to the maximum in the magnetic field in the holes, as shown in FIG. 6. The spatial distribution of the fields near the resonance are shown in FIG. 7. For the considered lossless system, the electric and magnetic fields tend to infinity at the resonance. In any real metal film, the resonance fields acquire some finite values limited by losses. Yet, if the losses are relatively small because, for example, of a strong skin effect, the resonance field remains very large leading to the EOT, even for very small holes, with $D \ll \lambda$.

For "deep" holes with h>2a, the resonances lose their k-periodicity. The positions of the electric and magnetic resonances, $k_{jE}$ and $k_{jH}$ respectively, can be found, in this case, from the following equations:

$$k_{jE} \cot(3ak_{jE}) + \sqrt{\kappa^2 - k_{jE}^2} \tanh\left[\left(\frac{h}{2} - a\right)\sqrt{\kappa^2 - k_{jE}^2}\right] = 0, \tag{36}$$

and $$\sqrt{\kappa^2 - k_{jH}^2} \tan(3ak_{jH}) + k_{jH}\tanh\left[\left(\frac{h}{2} - a\right)\sqrt{\kappa^2 - k_{jH}^2}\right] = 0, \tag{37}$$

As follows from these equations, the electric and magnetic resonances merge together with increasing the film thickness h. Therefore, one has an interesting system, with the electric and magnetic fields acquiring large values at the same points.

The transmittance for a metal film with deep holes can be represented in the following form:

$$T = \sum_j \frac{4p^2\sin^4(2ak_j)}{(k-k_j+\Delta_j)^2\Gamma_j^2 + 4p^2\sin^4(2ak_j)}, \quad (38)$$

where $$\Delta_j = \frac{k_j p(k_j^2 - \kappa^2)\sin(4ak_j)}{2(h+4a)k_j^3 - (h+10a)k_j\kappa^2 +}, \quad (39)$$
$$\kappa^2[(h-2a)k_j\cos(6ak_j) + 2\sin(6ak_j)]$$

$$\Gamma_j = \frac{2(h+4a)k_j^3 - (h+10a)k_j\kappa^2 + \kappa^2[(h-2a)k_j\cos(6ak_j) + 2\sin(6ak_j)]}{2\sqrt{2}\,k_j(k_j^2 - \kappa^2)}. \quad (40)$$

Figure 8:
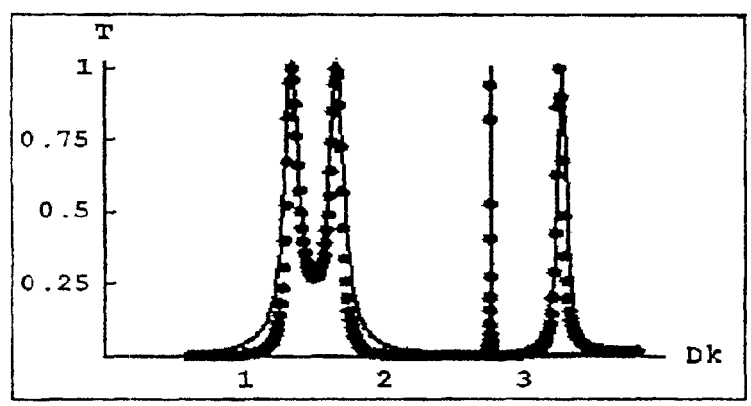
FIG. 8 shows transmittance through deep holes (h<2a); a/D=0.6, h/D=1.45, p=0.1; continuous line is by resonance approximation (Eq. (38)), points line calculated by Eq. (28).

The resonance wavevector $k_j$ in these equations takes values $k_{jE}$ and $k_{jH}$ given by Eqs. (36) and (37), respectively. Thus obtained T(k) is shown in FIG. 8. One can see that the k behavior of the transmittance can be rather peculiar when the thickness of the film increases: the peaks move, merge together, etc. Note that Eq. (38) holds when the neighboring electric and magnetic maxima do not overlap much; otherwise, the general Eq. (28) should be used to calculate the transmittance using the known Ohmic parameters $u_m$, $u_h$, $v_m$, and $v_h$.

Figure 9A:
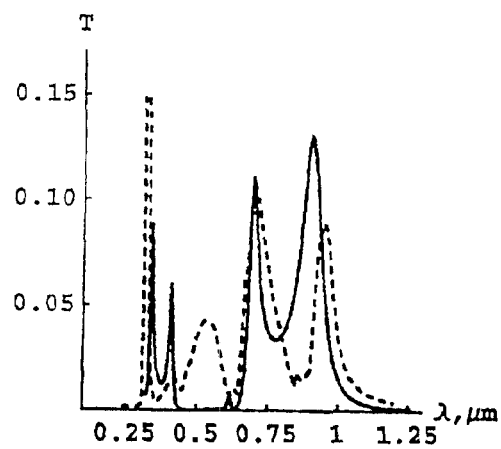
FIG. 9 shows extraordinary transmittance through a regular array of holes perforated in silver film points line is from the experiment in Ebbesen, et al., infra, bold line is calculated from a=0.09 $\mu$m, D=0.15 $\mu$m, h=0.2 $\mu$m, b=0.6 $\mu$m, p=0.049.
Figure 9B:
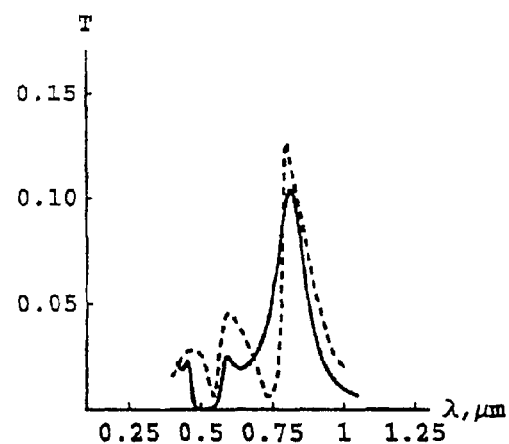
Figure 10A:
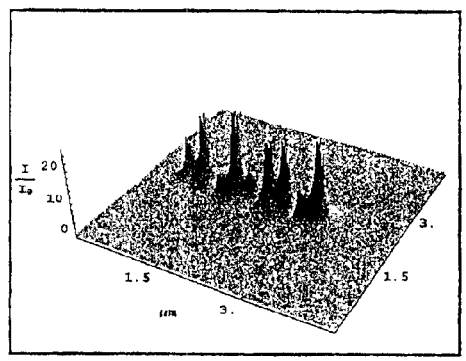
FIGS. 10($a$)–($d$) show photonic nanocircuiting with metal-holes systems ($a$); line plasmonic waveguide ($b$); fork waveguide, first hole is excited (c); and plasmonic switch (center hole in the top of "T") is excited (d); diameter of holes is 150 nm, film thickness is 200 nm, distance between the holes is 300 nm; excitation wavelength of light is 780 nm.
Figure 10B:
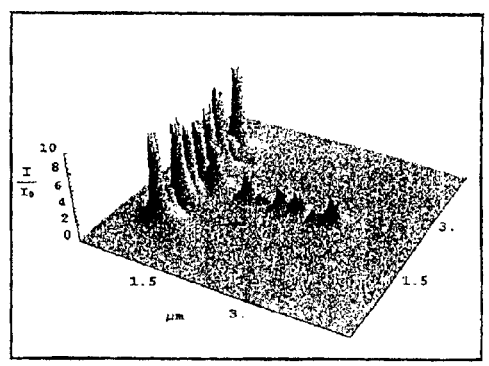
Figure 10C:
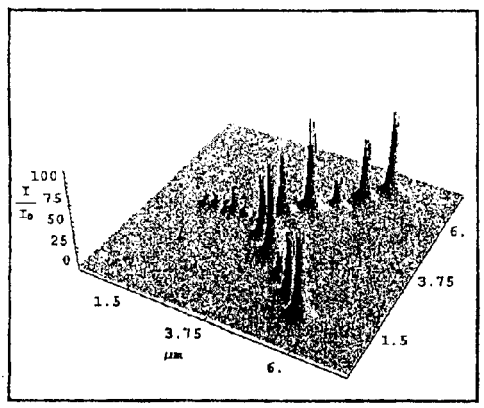
Figure 10D:
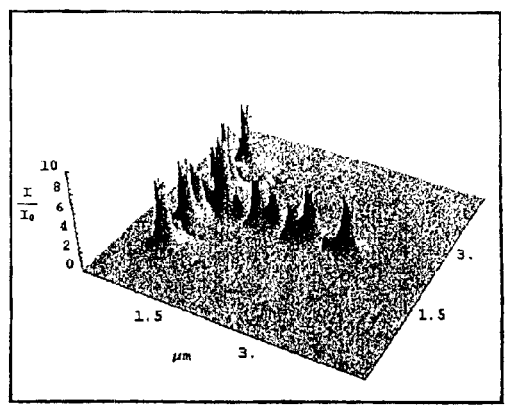

The results obtained can be easily verified in the microwave and GHz ranges, because in this case it is far easier (than in the optical range) to control the system parameters and losses are less important. The proper holes can be drilled through, for example, silver or aluminum slab. See, e.g., A. P. Hibbins, et al., *Appl. Phys.* 86, 1791 (1999). In the optical range, losses cannot be neglected, even for silver films providing largest field enhancement. The losses become most important in the resonance when the local field are strongly enhanced. Since the resonance fields are concentrated in the holes it is enough to take into account losses inside the holes only. Consider a hole as a wave guide with finite losses, Landau, et al., supra, by taking into account the actual silver dielectric permittivity, D. J. Nash, et al., *J. Mod. Opt.* 43, 81(1996); *J. Mod. Opt.* 46, 1793 (1999); P. V. Ashrit, et al., *Appl. Phys.* 74, 602 (1993); and H. Raether, *Surface Plasmons on Smooth and Rough Surfaces and on Gratings* (Springer, Berlin, 1988). When the skin depth δ is much smaller than the hole diameter D (for silver δ~10 nm in the optical range), the losses result in the appearance of the imaginary part in the wavevector k in Eqs. (36) and (37). In actual calculations one preferably sets the distance from the reference plane as a, which is a single fitting parameter in the theory, equal to a=0.6D in agreement with previous estimates for thin films. Shubin, et al., supra; Sarychev et al., supra (1994); Sarychev, et al., supra (1995); Levy-Nathansohn, et al., supra; and Lagarkov, et al., supra. The thus obtained transmittance for an array of nano-holes in a silver film is in qualitative agreement with the well-known experiments, Ebbesen, et al., supra, as shown in FIG. 9. The only evident discrepancy between the theory and experiments is a short wavelength peak, which results from the excitation of surface plasmon polaritons, which are propagating surface waves that can occur for a periodic array of nano-holes. By taking into account the excitation of SPPs, in this case, one can also reproduce the short wavelength peaks in the transmittance. It is important to emphasize that, in accord with the considerations above, the long wavelength peaks in the EOT are not sensitive to the periodicity.

Localized vs. Propagating Surface Plasmons. The results obtained above do not actually depend on the arrangement of the holes and require only that the surface concentration is small, p<<1. Thus Eqs. (35) and (38) hold for the holes arranged into a regular lattice since the MG approach works in this case as well. See A. K. Sarychev, et al., *Phys. Rep.* 335, 275 (2000). Below is considered the square lattice, with the period b so that the hole concentration $p=\pi D^2/4b^2$. There are new properties for the transmittance through the square array of holes in a metal film. Apart from the resonances given by Eqs. (35) and (38), new resonances can appear resulting from the excitation of propagating SPPs. The SPP is characterized by the wave vector $k_p$, in contrast to the localized resonance fields discussed above. When one of the spatial constants $B_{n_1 n_2} = b/\sqrt{n_1^2 + n_2^2}$ ($n_1, n_2 = 0, 1, 2 \ldots$; $n_1 \cdot n_2 \neq 0$) of the lattice coincides with the SPP wavelength $\lambda_p = 2\pi/k_p$, the SPP is efficiently excited on the surface of the film. Since the film is optically thick the SPP is excited first on the back interface of the film. Yet, eventually, it spreads over on both sides of the film, so that SPPs on both interfaces, front and back, of the film are excited. There is a straightforward analogy between the SPPs on the two sides of the film and two identical oscillators coupled together. The coupling can be arbitrarily weak, nevertheless, if one pushes the first oscillator, then, in some period of time (which depends on the coupling strength) the second oscillator starts to oscillate with the same amplitude as the first oscillator. By the same token, the two SPPs on the different sides of the film will have eventually the same amplitudes. When an SPP propagates on the front side of the film it interacts with the holes and, as a result, converts its energy back to the plane wave re-emitted from the film. Therefore, at the plasmon resonance, the film becomes almost transparent, regardless of its thickness.

To reiterate, the SPP interacts "twice" with the holes to result in the resonance transmittance. Therefore, the transmittance amplitude t is proportional to $p^2$ and, as result, the width of maxima in the transmittance $T=|t|^2$ is proportional to $p^4$, in contrast to the $p^2$ width given by Eqs. (35) and (38). Such "thin" resonances almost fade away when losses are taken into account. Indeed, in FIG. 9 the peaks at $\lambda \cong 0.6$ μm and $\lambda \cong 0.6/\sqrt{2}\,0.4$ μm, which are associated with the SPP excitation, are rather small (the spatial period of the lattice of the holes was b=0.6 μm). The situation changes dramatically when the SPP resonance coincides with one of the MG resonances considered above, i.e., when $\lambda_p = B_{n_1 n_2}$, and, simultaneously, $u_m = -u_h$ or $v_m = -v_h$. Such "double" resonance occurs in the system at the wavelength of the incident wave λ=0.3 μm and results in the prominent peak in the transmittance observed in the experiments of Ebbesen, et al., supra (see FIG. 9).

Above, the case of a metal film being irradiated homogeneously by a plane electromagnetic wave was considered. When only one of the holes is illuminated by light source, for example, using a nanometer-size probe of near-field scanning optical microscope, at the resonance, electric and/or magnetic fields spread out from the illuminated hole toward other holes because of interactions between the holes via plasmons. Such holes can be arranged into any desired structures that can localize light and guide the propagation of the electromagnetic energy along the structures (see FIG. 10). Such nano-engineered structures can be used as integrated elements in various optoelectronic and photonic devices, including most sophisticated ones, such as optical computers.

Plasmon Modes in Metal Nanowires and Their Use for Molecule Sensing. Recently, the problem of EM field distribution for long and thin nanometer-sized needles (nanowires) has attracted growing interest, namely metal needles whose diameter is much smaller than the wavelength of incident light, and whose length is of the order of the wavelength. There are several numerical methods available for finding field distributions for objects of arbitrary shapes. The present invention uses a special modification of the discrete-dipole approximation (DDA), which employs the intersecting effective spheres for finding the field distribution. By using this approach one can simulate the field distribution for individual nm-sized metal needles and for a percolation composite formed by such needles. For individual needles, the surface plasmon polaritons (SPPs) can be excited, resulting in large local fields. For percolation composites formed by the needles, simulations suggest the existence of localized plasmon modes and strong local field enhancement associated with these modes. Accordingly, one can produce a left-handed nanowire composite.

First consider long needles, which are also be referred to herein as wires. The ratio of the needle length and diameter (the aspect ratio) can vary from 10 to 1000. In the preferred approach of the invention, one approximates a long needle by chains of small spheres. In simulations, one can use four long chains parallel to each other (see FIG. 17); this, in particular, allows one to take into account the skin effect.

Suppose that the system is illuminated by a monochromatic plane wave $E_{inc}(r,t)=E^{(0)} \exp(i\omega t - ikr)$. The discussion below omits the common factor for all time-varying terms, $\exp(i\omega t)$. Each spherical particle is then represented by a dipole located at the point $r_i$ (the center of the sphere) with dipole moment $d_i$. This dipole moment is proportional to the local EM field, which is a superposition of the incident EM field and the field "scattered" by all other dipoles of the system. Thus, to find the individual dipole moments one needs to solve the following coupled-dipole equations (CDEs).

$$d_i = \alpha_0 [E_{inc}(r_i) + \Sigma_{j \neq i} G(r_i - r_j) d_j], \quad (41)$$

where $G(r_i - r_j) d_j$ represents the EM field resulting from dipole j at the position of dipole i, and G is the regular part of the free-space dyadic Green function defined as $$G_{\alpha\beta} = k^3 [A(kr)\delta_{\alpha\beta} + B(kr) r_\alpha r_\beta / r^2], \quad (42)$$

$$A(x) = [x^{-1} + ix^{-2} - x^{-3}] \exp(ix),$$

$$B(x) = [-x^{-1} - 3ix^{-2} + 3x^{-3}] \exp(ix),$$

with $G d = G_{\alpha\beta} d_\beta$. The Greek indices represent the Cartesian components of vectors, and the summation over the repeated indices is implied.

The CDEs approach allows one to find the scattering and absorption of light by odd-shaped dielectric particles. In this approach, the individual dipoles are placed into the cubic lattice within the object, with the lattice period of a. The polarizability of an individual dipole was chosen to be equal to the polarizability of a small sphere with radius $R_m$. The radius $R_m$ is chosen so that the total volume of all spheres is equal to the volume of the object. Note, that the two neighboring particles have to geometrically intersect, in this case, because $$a/R_m = (4\Pi/3)^{1/3} \approx 1.612 < 2. \quad (43)$$

The polarizability of individual dipoles is given by a well-known Clausius-Mossotti relation with the radiative correction:

$$\alpha_0 = \alpha_{LL} / [1 - i(2k^3/3)\alpha_{LL}] \quad (44)$$

$$\alpha_{LL} = R_m^3 (\in -1)/(\in +2) \quad (45)$$

where $\in$ is the dielectric constant of the material (the host is assumed to be vacuum), and $\alpha_{LL}$ is the Loretz-Lorenz polarizability without the radiation correction.

In our case the system is represented by long chains of "intersecting spheres." The "intersection ratio" $a/R_m$ for the infinite chain of the spherical particles should slightly differ from the one given by Eq. 43 in order to give the correct depolarization factors $$a/R_m \approx 1.688 \quad (46)$$

To find the field distribution around a metal needle we are solving the system of linear equations (!) with $\alpha_0$ defined in (44)–(45).

In the present simulations the lattice size was chosen to be 15 nm so that the total cross-section of the needle (2×2 particles) is 30 nm (see FIG. 17). Two different kinds of simulations were employed. Specifically, one can calculate the field distribution over an individual long needle for different angles of incidence of the excitation wave. One can also calculate the field distribution over a percolation composite made from randomly distributed needles. In all the present simulations the wavelength of incident light is 540 nm.

This specification first addresses the question of the EM field distribution for a single metal needle. For this kind of simulation it is preferred to use a very long needle with the length of approximately 15 $\mu$m. In all pictures obtained one can clearly see the interference pattern between the incident wave and SPP wave in the needle (see FIG. 18). This pattern strongly depends on the angle between the needle and the wavevector of the incident wave (note that the needle and the wavevector of the incident light always lie in the same plane). In FIG. 18(a) the wavevector of the incident light is parallel to the needle. In FIGS. 18(b) and (c) the angle between them is 30 and 60 degrees, respectively. FIG. 18(d) shows the field distribution for the case when the wavevector of the incident light is perpendicular to the needle (in this case the electric field is parallel to the needle).

Figure 19A:
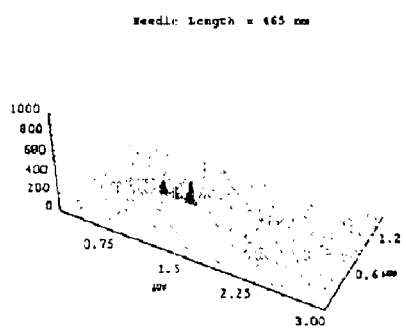
FIGS. 19(a)–(f) illustrate plasmon resonance in a "short" needle; the wavelength of incident light is 540 nm, the angle of incidence is 30°, and the needle lengths are 465 nm (FIGS. 19(a) and (c)), 480 nm (FIGS. 19(b) and (d)), and 495 nm (FIGS. 19(e) and (f)).
Figure 19B:
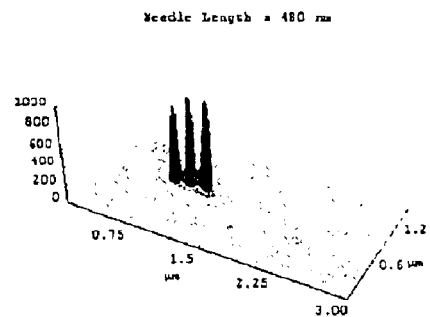
Figure 19C:
Figure 19D:
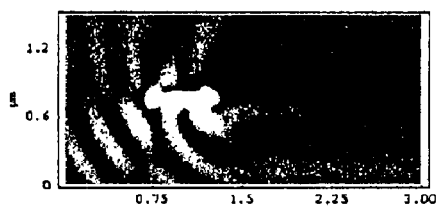
Figure 19E:
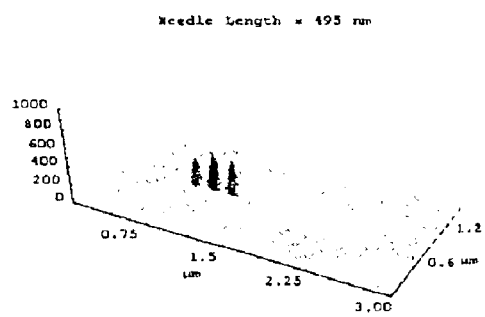
Figure 19F:
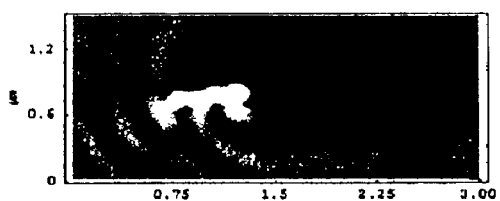

The simulations suggest the existence of plasmon resonances in the metal needle. To check this assumption one can vary the needle length, keeping the wavelength of the incident light and the angle of incidence both fixed. The angle of incidence was chosen to be 30 degrees. To save the computational time used in these calculations, "short" needles were employed with the length close to the wavelength (FIGS. 19a, b, and c). Note that the length and diameter ratio, in this case, is close to 15; so it is still much larger than 1. The results show the existence of the resonance when the needle length is an integer of the half of the plasmon wavelength. Also, one obtains strong dependence of the resonant needle length on the angle of incidence. The resonances are very sharp with the peak intensity enhancement on the order of $10^3$. The enhanced local fields allow one to perform surface-enhanced spectroscopy and molecule sensing using metal nanowires.

The results were checked for different angles of incidence and similar resonant behavior was found. Simulations were also conducted with the length of the needle being constant, whereas the wavelength of the incident light was varying; the obtained results show similar resonant behavior.

This specification now discusses the EM field distribution over randomly distributed metal needles on the on the plane. The concentration of needles was chosen to be equal to the percolation (conductivity) threshold. The existence of localized plasmon modes for metal-dielectric percolation films (also referred to as semicontinuous metal films) was recently predicted by Sarychev and Shalaev and experimentally verified in experiments performed by a French team (S. Ducourtieux, et al., *Phys. Rev. B* 64 (2001)). In semicontinuous metal films local fields are shown to be extremely enhanced in small nm-sized areas. One can anticipate similar kinds of behavior in a percolation 2D system composed of needles. Percolation threshold for the "needle composite" is known to be equal to b/l, where b is the needle diameter and l is the needle length (A. N. Lagarkov, et al., *Phys. Rev. B* 53, 10 (1996)).

Figure 20A:
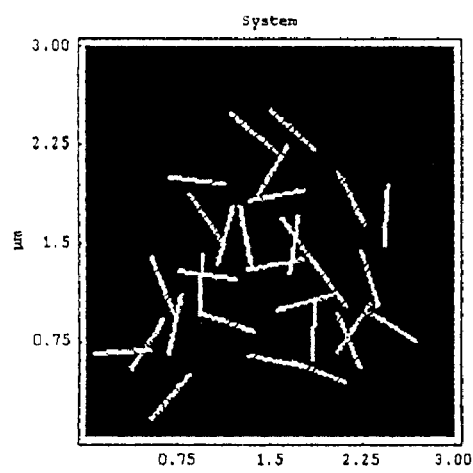
FIGS. 20(a)–(c) show percolation composite formed by metal needles (a); the EM field distribution for the composite (b); and NSOM image simulation (c).
Figure 20B:
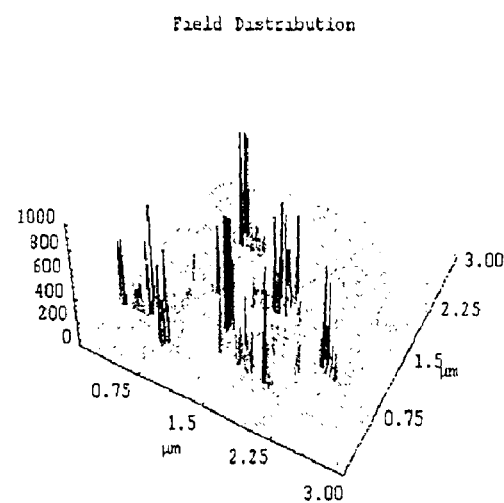
Figure 20C:
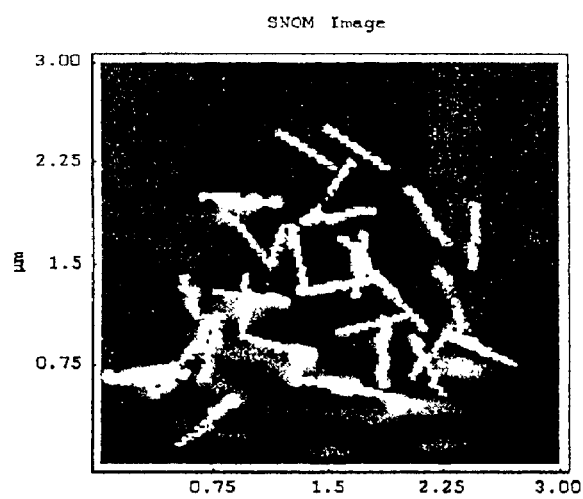

Via the present numerical simulations the present specification considered the "needle composite" exactly at the percolation threshold. The length of individual needles in the composite was chosen to be equal to the resonant needle length for the case when the electric field in the incident wave is parallel to the needle. The results are presented in FIG. 20. In FIG. 20(*a*), one sees the system of needles used for simulations. The spatial EM field distribution is presented in FIG. 20(*b*). In FIG. 20(*c*), one sees results of simulations for the near-field scanning optical microscope (NSOM) image. As seen in the figures, the simulation results suggest the existence of localized plasmon modes in the system, with the peak intensity enhancement on the order of $10^3$ in the near field.

Left-Handed Nanowire Composites. Shultz and Smith, following and further developing ideas of Pendry have recently demonstrated a new material, having in the GHz spectral range permetivity, $\in$, and magnetic permeability, $\mu$, both negative (D. R. Smith et al, *Phys. Rev. Lett.* 84, 4184 (2000)). Such material should also have negative refractive index, $n=-\sqrt{(\in\mu)}$. As first predicted by Veselago, the electromagnetic plane wave in such media propagates in the direction opposite to the flow of energy. Such materials are often called "left-handed" since the three vectors E, H, and k inside them form a left-handed system. These materials are anticipated to have a number of very unusual properties, which include inverse Doppler shift, inverse Snell effect and reversed Cerenkov radiation. A plane slab of such material can focus a light beam.

Figure 21A:
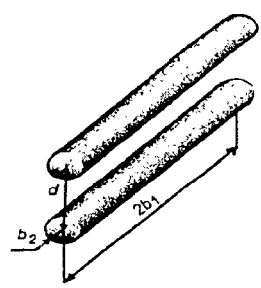
FIGS. 21(a)–(b) illustrates a system of two parallel nanowires (a) and a composite comprising such pairs of parallel nanowires (b).
Figure 21B:
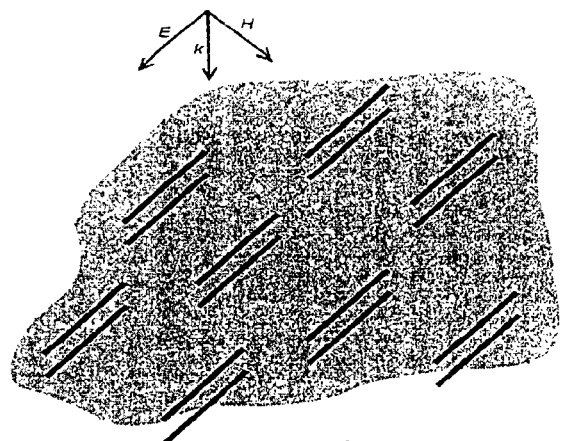

The present invention is of a material comprising pairs of nanowires parallel to each other. Such material can have a negative refractive index in the near IR and the visible spectral ranges. Consider a thin layer of material, composed from pairs of nanowires parrallel to each other. The length of individual nanowires is $2b_1$, their diameter is $2b_2$, and the distance between the nanowires in the pair is d. The needles are assumed to be embedded into host with dielectric constant $\in_d$. Consider the case of closely placed long nanowires so that $b_2 \ll d \ll b_1$. The incident wave propagates normal to the composite surface so that the electric field is parallel to the nanowires, while the magnetic field is perpendicular to the nanowire pairs (see FIG. 21).

Consider the macroscopic optical characteristics of such material, namely, the effective dielectric constant $\in$ and effective magnetic permeability $\mu$. To take into account a skin-effect we introduce the function[3] $f(\Delta)=[(1-i)/\Delta]J_1[(1+i)\Delta]/J_0[(1+i)\Delta]$, where parameter $\Delta=b_2\sqrt{(2\Pi\sigma_m\omega)}/c \gg 1$ represents the ratio of nanowire radius and the skin depth ($\sigma_m$ is bulk metal conductivity).

To find the magnetic permeability of the composite one must first find the magnetic moment $m_H$ of the individual two-needle system. Approximate such pair by two parallel infinite wires so that the telegraph equation can be applied. The time-varying magnetic field excites the currents in the nanowires in the pairs, with the displacement currents between the wires "closing" the electric circuit. Thus, the currents induced by the magnetic field move in opposite directions in the wires in the pair. Using the telegraph equation one arrives at the following expression for the magnetic moment of the pair.

$$m_H=2Hb^3C_2(kd)^2[\tan(gb_1)-gb_1]/(gb_1)^3, \quad (47)$$

where $C_2=\in_d/[4\ln(d/b_2)]$ is the system's capacity per unit length, and parameter g is given by $g=k\sqrt{(\in_d+i\in_d/[2\Delta^2 f(\Delta)\ln(d/b_2)]}$.

The incident electric field is parallel to the wires, so it excites equal currents in the two wires in the pair, which can be considered as independent. The total dipole moment for the two nanowires in the pair is given by $$d_E=(\tfrac{2}{3})b_1b_2{}^2 f(\Delta)E\in_m/[1+f(\Delta)\in_m(b_2/b_1)^2\ln(1+\in_d b_1/b_2)\cos\Omega], \quad (48)$$

where the dimensionless frequency is given by $\Omega^2=(b_1 k)^2[\ln(b_1/b_2)+i\sqrt{\in_d}kb_1]/\ln(1+\in_d b_1/b_2)$.

Using the magnetic and dipole moments above, one can find the effective dielectric constant and magnetic permeability for the 2D nanoneedle composite film $$\mu=1+(4p/b_1b_2d)\,(m_H/H) \quad (49)$$

$$\in=1+(4p/b_1b_2d)\,(d_E/E),$$

where p is surface metal concentration.

Figure 22A:
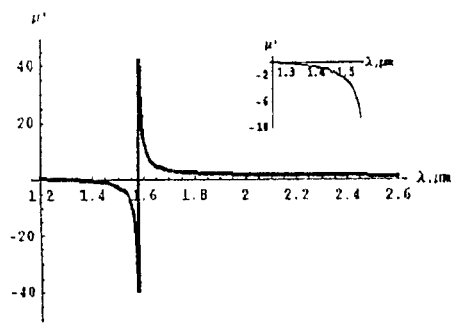
FIGS. 22(a)–(c) show the real parts of the effective magnetic permeability (a), dielectric permittivity (b), and refractive index (c) for the composite shown in FIG. 5(b); surface metal concentration p=0.1; other parameters are $b_1$=350 nm, $b_2$=5 nm, and d=150 nm.
Figure 22B:
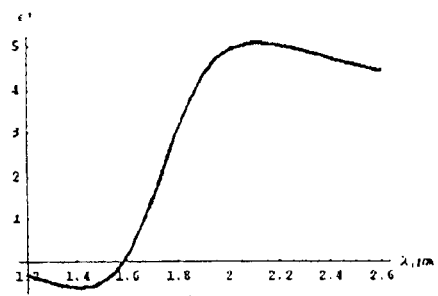
Figure 22C:
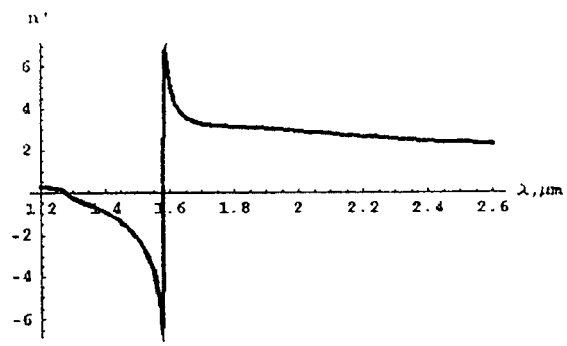

The macroscopic parameters of the composite, which are calculated using the formulas above, are shown in FIG. 22. As seen in the figure, both permittivity and magnetic permeability have the resonant structure. Note that the resonance position (and therefore the spectral range where the material refractive index is negative) is determined by parameters $b_1$, $b_2$, and d. In FIG. 22 is illustrated the left-handed material in a vicinity to the telecommunication wavelength 1.5 $\mu$m. By varying the parameters $b_1$, $b_2$, and d the negative-refraction spectral range can be moved to the visible part of the spectrum.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for optically controlling characteristics of an optically thick metal film, the method comprising the steps of:
   providing a film with an optical nonlinearity but not having fabricated periodic perforation; and
   directing at the film at least two control light beams at angles $\pm\Theta$ with respect to normal;
   thereby inducing light transmittance through the film, the induced light transmittance having two or more stable states, any of which states may be induced.

2. The method of claim 1 wherein the providing step comprises providing one or more layers of highly nonlinear material on one or more sides of the film.

3. The method of claim 2 wherein the providing step comprises providing one or more photorefractive semiconductor layers on one or more sides of the film.

4. The method of claim 1 wherein the providing step comprises providing inclusions of highly nonlinear material within the film.

5. The method of claim 4 wherein the providing step comprises providing photorefractive semiconductor inclusions within the film.

6. The method of claim 1 wherein the directing step comprises directing two or more control beams to each side of the film.

7. The method of claim 1 wherein the directing step comprises switching on and off the control beams.

8. The method of claim 1 additionally comprising the step of providing a modulation of the control beams.

9. The method of claim 1 wherein the providing step comprises providing non-periodical nanoholes to the film.

10. An optical logic element operating according to the method of any of claims 1–8 or 9.

11. The optical logic element of claim 10, wherein said element is selected from the group consisting of optical gates, optical switches, optical transistors, optical modulators, and optical filters.

12. The optical logic element of claim 11 wherein said element is an optical gate operating by switching on and off the control beams.

13. The optical logic element of claim 11 wherein said element is an optical modulator which modulates the control beams.

14. The optical logic element of claim 11 wherein said element is an optical filter device and wherein a magnetic field provides tunability.

15. The optical logic element of claim 11 wherein said element is an optical filter device and wherein said device is controlled by light beams with different wavelengths.

16. An optical device for selecting and controlling single and small number of photons operating according to the method of any of claims 1–8 or 9.

17. A single-photon turnstile device operating according to the method of any of claims 1–8 or 9.

18. A quantum nondemolition photon detector operating according to the method of any of claims 1–8 or 9.

19. A quantum computer device operating according to the method of any of claims 1–8 or 9.

20. A quantum-bit memory device operating according to the method of any of claims 1–8 or 9.

21. An optical device for strong quantum correlation between single photons operating according to the method of any of claims 1–8 or 9.

22. A quantum teleportation device operating according to the method of any of claims 1–8 or 9.

23. A method for optically controlling characteristics of an optically thick metal film, the method comprising the steps of:

providing a film with an optical nonlinearity but not having fabricated periodic perforation by providing non-periodic nanoholes to the film; and directing at the film at least two control light beams at angles $\pm\Theta$ with respect to normal;

thereby inducing light transmittance through the film.

24. The method of claim 23 wherein the providing step further comprises providing one or more layers of highly nonlinear material on one or more sides of the film.

25. The method of claim 24 wherein the providing step further comprises providing one or more photorefractive semiconductor layers on one or more sides of the film.

26. The method of claim 23 wherein the providing step further comprises providing inclusions of highly nonlinear material within the film.

27. The method of claim 26 wherein the providing step further comprises providing photorefractive semiconductor inclusions within the film.

28. The method of claim 23 wherein the directing step comprises directing two or more control beams to each side of the film.

29. The method of claim 23 wherein the directing step comprises switching on and off the control beams.

30. The method of claim 23 additionally comprising the step of providing a modulation of the control beams.

31. The method of claim 23 wherein the induced light transmittance has two or more stable states, any of which states may be induced.

32. An optical logic element operating according to the method of any of claims 23–31.

33. The optical logic element of claim 32 wherein said element is selected from the group consisting of optical gates, optical switches, optical transistors, optical modulators, and optical filters.

34. The optical logic element of claim 33 wherein said element is an optical gate operating by switching on and off the control beams.

35. The optical logic element of claim 33 wherein said element is an optical modulator which modulates the control beams.

36. The optical logic element of claim 33 wherein said element is an optical filter device and wherein a magnetic field provides tunability.

37. The optical logic element of claim 33 wherein said element is an optical filter device and wherein said device is controlled by light beams with different wavelengths.

38. An optical device for selecting and controlling single and small number of photons operating according to the method of any of claims 23–31.

39. A single-photon turnstile device operating according to the method of any of claims 23–31.

40. A quantum nondemolition photon detector operating according to the method of any of claims 23–31.

41. A quantum computer device operating according to the method of any of claims 23–31.

42. A quantum-bit memory device operating according to the method of any of claims 23–31.

43. An optical device for strong quantum correlation between single photons operating according to the method of any of claims 23–31.

44. A quantum teleportation device operating according to the method of any of claims 23–31.

* * * * *